US011826411B2

United States Patent
Martín Montañes et al.

(10) Patent No.: US 11,826,411 B2
(45) Date of Patent: Nov. 28, 2023

(54) COMPOSITIONS FOR USE AS A PROPHYLACTIC AGENT TO THOSE AT RISK OF INFECTION OF TUBERCULOSIS, OR AS SECONDARY AGENTS FOR TREATING INFECTED TUBERCULOSIS PATIENTS

(71) Applicants: UNIVERSIDAD DE ZARAGOZA, Saragossa (ES); BIOFABRI S.L., Pontevedra (ES)

(72) Inventors: Carlos Martín Montañes, Saragossa (ES); Juan Ignacio Aguiló Anento, Saragossa (ES); Jesús Ángel Gonzalo Asensio, Saragossa (ES); Dessislava Vaneva Marinova, Saragossa (ES); Santiago Uganda Maíz, Saragossa (ES); Esteban Rodríguez Sánchez, Pontevedra (ES); Eugenia Puentes Colorado, Pontevedra (ES); Concepción Fernández Álvarez-Santullano, Pontevedra (ES)

(73) Assignees: UNIVERSIDAD DE ZARAGOZA, Saragossa (ES); BIOFABRI S.L., Pontevedra (ES)

( * ) Notice: Subject to any disclaimer, the term of this patent is extended or adjusted under 35 U.S.C. 154(b) by 634 days.

(21) Appl. No.: 16/971,248

(22) PCT Filed: Feb. 19, 2019

(86) PCT No.: PCT/EP2019/054106
§ 371 (c)(1),
(2) Date: Aug. 19, 2020

(87) PCT Pub. No.: WO2019/158779
PCT Pub. Date: Aug. 22, 2019

(65) Prior Publication Data
US 2023/0165948 A1    Jun. 1, 2023

(30) Foreign Application Priority Data
Feb. 19, 2018   (EP) .................................... 18382097

(51) Int. Cl.
*A61K 39/02*   (2006.01)
*A61K 39/04*   (2006.01)
*A61P 37/04*   (2006.01)
*C12N 1/20*    (2006.01)
*A61K 39/00*   (2006.01)

(52) U.S. Cl.
CPC .............. *A61K 39/04* (2013.01); *A61P 37/04* (2018.01); *C12N 1/20* (2013.01); *A61K 2039/522* (2013.01); *C12N 2500/16* (2013.01); *C12N 2500/32* (2013.01); *C12N 2500/34* (2013.01); *C12N 2500/35* (2013.01)

(58) Field of Classification Search
None
See application file for complete search history.

(56) References Cited

U.S. PATENT DOCUMENTS

| 8,287,886 B2    | 10/2012  | Montanes et al.          |
| 10,673,347 B2   | 6/2020   | Sarnago Andía et al.     |
| 11,142,734 B2   | 10/2021  | Fernández Ledesma et al. |
| 11,224,744 B2   | 1/2022   | Sarnago Andía et al.     |
| 2019/0366365 A1 | 12/2019  | Santamaría Ramiro et al. |
| 2021/0340196 A1 | 11/2021  | Anel Bernal et al.       |

FOREIGN PATENT DOCUMENTS

| CN | 104324365 A    | 2/2015  |
| GB | 1108956 A      | 4/1968  |
| WO | 98/44096 A2    | 10/1998 |
| WO | 2018/006939 A1 | 1/2018  |

OTHER PUBLICATIONS

Ungar et al Br. Med. J. 1962, 2(5312): 1086-1089.*
Sigma-Aldrich, "Product Information: M0178 Middlebrook 7H9 Broth Base," 2013, 1 page.
HiMedia Laboratories, "Sautons Fluid Medium Base," Technical Data, 2011, 2 pages.
Extended European Search Report for European Application No. 18382097.6, dated Sep. 25, 2018, 16 pages.
International Search Report for International Application No. PCT/EP2019/054106, dated Apr. 17, 2019, 5 pages.
Lyon et al., "Effect of Tween 80 on the Growth of Tubercle Bacilli in Aerated Cultures," *J. Bacteriol.* 86:280-284, 1963.
Marinova et al., "MTBVAC from discovery to clinical trials in tuberculosis-endemic countries," *Expert Review of Vaccines* 16(6):565-576, 2017.
Arbues et al., "Construction, characterization and preclinical evaluation of MTBVAC, the first live-attenuated *M. tuberculosis*—based vaccine to enter clinical trials," *Vaccine* 31:4867-4873, Aug. 2013.

(Continued)

*Primary Examiner* — Jennifer E Graser
(74) *Attorney, Agent, or Firm* — SEED INTELLECTUAL PROPERTY LAW GROUP LLP

(57) ABSTRACT

The present invention refers to a freeze-dried composition consisting of an isolated microorganism belonging to the *Mycobacterium tuberculosis* complex, preferably a *M. tuberculosis* clinical isolate, more preferably *M. tuberculosis* clinical isolate, characterized in that it comprises a PhoP- phenotype by the inactivation by a genetic deletion of the Rv0757 gene and the deletion of a second gene, Rv2930 (fadD26), that prevents PDIM production (PDIM- phenotype) (the MTBVAC strain), and sucrose and sodium glutamate as stabilizers or excipients. The present invention further refers to the reconstituted composition obtained by adding water, preferably sterilized water for injection, to the freeze-dried composition as well as uses thereof, in particular for use as a prophylactic agent to those at risk of infection with *M. tuberculosis* or those at risk of developing tuberculosis disease, or as secondary agents for treating infected tuberculosis patients.

5 Claims, 13 Drawing Sheets
Specification includes a Sequence Listing.

(56) References Cited

OTHER PUBLICATIONS

Arbués Arribas, "Construction and characterization of a new generation of phoP—based vaccines against tuberculosis," doctoral dissertation, Universidad de Zaragoza, Zaragoza, Spain, 2010. (157 pages).
Arnoldussen et al., "BCG vaccination and allergy: A systematic review and meta-analysis," *J Allergy Clin Immunol* 127(1):246-253, 2011.
Behr, "BCG—different strains, different vaccines?" *The Lancet Infectious Diseases* 2:86-92, Feb. 2002.
Braunstein et al., "Why Wait? The Case for Treating Tuberculosis with Inhaled Drugs," *Pharmaceutical Research* 36(166):1-6, 2019, (6 pages).
Camacho et al., "Analysis of the Phthiocerol Dimycocerosate Locus of *Mycobacterium tuberculosis*," *The Journal of Biological Chemistry* 276(23):19845-19854, Jun. 8, 2001.
Camacho et al., "Identification of a virulence gene cluster of *Mycobacterium tuberculosis* by signature-tagged transposon mutagenesis," *Molecular Microbiology* 34(2):257-267, 1999.
Choi et al., "Therapeutic effects of BCG vaccination in adult asthmatic patients: a randomized, controlled in trial," *Ann Allergy, Asthma, & Immunol* 88:584-591, 2002.
Cole et al., "Deciphering the biology of *Mycobacterium tuberculosis* from the complete genome sequence," *Nature* 393:537-544, Jun. 11, 1998.
Cox et al., "Complex lipid determines tissue-specific replication of *Mycobacterium tuberculosis* in mice," *Nature* 402:79-83, Nov. 4, 1999.
Diaz et al., "Comparative Metabolomics between *Mycobacterium tuberculosis* and the MTBVAC Vaccine Candidate," *ACS Infect. Dis.* 5:1317-1326, 2019.
Erb et al., "Infection of Mice with *Mycobacterium bovis*—Bacillus Calmette-Guérin (BCG) Suppresses Allergen-induced Airway Eosinophilia," *J Exp. Med.* 187(A):561-569, Feb. 16, 1998.
Girodet et al., "Alternative Macrophage Activation Is Increased in Asthma," *Am J Respir Cell Mol Biol* 55(4):467-475, Oct. 2016.
Gonzalo-Asensio et al., "MTBVAC: Attenuating the Human Pathogen of Tuberculosis (TB) Toward a Promising Vaccine against the TB Epidemic," *Frontiers in Immunology* 8:1803, Dec. 2017, (8 pages).
Guerra-Maupome et al., "Aerosol vaccination with Bacille Calmette-Guerin induces a trained innate immune phenotype in calves," *PLoS ONE* 14(2):e0212151, Feb. 22, 2019, (16 pages).
Holgate, "Innate and adaptive immune responses in asthma," *Nature Medicine* 18(5):673-683, May 2012.
Holgate et al., "Asthma," *Nat Rev Dis Primers* 1:15025, 2015. (22 pages).
Kwok et al., "Direct ex vivo analysis of allergen-specific CD4+ T cells," *J Allergy Clin Immunol.* 725(6):1407-1409.e1, Jun. 2010.
Lagranderie et al., "*Mycobacterium bovis* BCG killed by extended freeze-drying reduces airway hyperresponsiveness in 2 animal models," *J Allergy Clin Immunol* 121(2):471-478, Feb. 2008.

Malaga et al., "Production of unmarked mutations in mycobacteria using site-specific recombination," *FEMS Microbiology Letters* 219:261-268, 2003.
Mills et al., "M-1/M-2 Macrophages and the Th1/Th? Paradigm," *J Immunol* 164:6166-6113, 2000.
Moreira et al., "Serum amyloid P attenuates M2 macrophage activation and protects against fungal spore-induced allergic airway disease," *J Allergy Clin Immunol* 126:112-121, 2010.
Murray et al., "Protective and pathogenic functions of macrophage subsets," *Nature Reviews Immunology* 11:123-131, Nov. 2011.
Obihara et al., "*Mycobacterium tuberculosis* infection may protect against allergy in a tuberculosis endemic area," *Clinical and Experimental Allergy* 36:10-16, 2006.
O'Hehir et al., "T Cell Epitope Peptide Therapy for Allergic Diseases," *Curr Allergy Asthma Rep* 16:14, Jan. 14, 2016, (9 pages).
Pavord et al., "Mepolizumab for severe eosinophilic asthma (DREAM): a multicentre, double-blind, placebo-controlled trial," *Lancet* 380:651-659, Aug. 18, 2012.
Saradna et al., "Macrophage Polarization and Allergic Asthma," *Transl Res.* 191:1-14, Jan. 2018.
Sarinho et al., "BCG scar diameter and asthma: A case-control study," *J Allergy Clin Immunol* 106:1199-1200, Dec. 2000.
Schrager et al., "Developing aerosol vaccines for *Mycobacterium tuberculosis*: Workshop Proceedings: National Institute of Allergy and Infectious Diseases, Bethesda, Maryland, USA, Apr. 9, 2014," *Vaccine* 33:3038-3046, 2015.
Spertini et al., "Safety of human immunization with a live-attenuated *Mycobacterium tuberculosis* vaccine: a randomized, double-blind, controlled phase I trial," *Lancet Respir Med*, p. 1-10, Nov. 16, 2015.
Stein et al., "Innate Immunity and Asthma Risk in Amish and Hutterite Farm Children," *N Engl J Med* 375(5):411-421, Aug. 4, 2016.
Strachan, "Hay fever, hygiene, and household size," *Br Med J* 299:1259-1260, Nov. 18, 1989.
Tameris et al., "Live-attenuated *Mycobacterium tuberculosis* vaccine MTBVAC versus BCG in adults and neonates: a randomized controlled, double-blind dose-escalation trial," *Lancet Respir Med* 7:757-770, Sep. 2019.
Tarancón et al., "*Mycobacterium tuberculosis* infection prevents asthma and abrogates eosinophilopoiesis in an experimental model," *Allergy* 74(12):2512-2514, Dec. 2019.
Trivedi et al., "Dissecting the Mechanism and Assembly of a Complex Virulence Mycobacterial Lipid," *Molecular Cell* 17:631-643, Mar. 4, 2005.
Tsujimura et al., "Effects of Mycobacteria Major Secretion Protein, Ag85B, on Allergic Inflammation in the Lung," *PLoS ONE* 9(9):el06807, Sep. 5, 2014.
Von Bubnoff et al., "Antigen-presenting cells in allergy," *J Allergy Clin Immunol* 108:329-339, 2001.
Von Mutius et al., "International patterns of tuberculosis and the prevalence of symptoms of asthma, rhinitis, and eczema," *Thorax* 55:449-453, 2000.
U.S. Appl. No. 17/764,127, filed Mar. 25, 2022.

* cited by examiner

Study outline
- 3 groups/10 guinea pigs males/±350 g
- 42 d.p.v daily monitoring and weekly weight
- On day 42 p.v necropsy and lesion assessment (Simon Clark, HPA)

Vaccines: 50 x SHD

Readout:
NO ANIMAL DIED

NO SIGNS OF TUBERCULOSIS INFECTION

BCG showed a sig. lower weight than MTBVAC and naïve groups

8/10 liver granulomatous lesions in BCG group vs 0/10 in MTBVAC group

Significant lower spleen/body wgt ratio in MTBVAC-WSL

5/8 culture+ samples from BCG, 0/5 culture neg samples from MTBVAC

- Long term stability study of MSL stored at -80° C
- Long term stability study of WSL stored at -30° C

A.

B.

COMPOSITIONS FOR USE AS A PROPHYLACTIC AGENT TO THOSE AT RISK OF INFECTION OF TUBERCULOSIS, OR AS SECONDARY AGENTS FOR TREATING INFECTED TUBERCULOSIS PATIENTS

FIELD OF THE INVENTION

This invention relates to pharmaceutical compositions, such as vaccines, and methods of making and using such compositions.

BACKGROUND OF THE INVENTION

Bacille Calmette-Guérin (BCG) vaccine is an attenuated strain of *Mycobacterium bovis*, the etiologic agent of tuberculosis (TB) in cattle. BCG was introduced for the first time into clinical use almost a hundred years ago, when in 1921 it was given orally to an infant whose mother had died of TB a day after delivery. The infant showed no adverse events to vaccination with BCG and importantly, did not develop TB. At that time, the oral route of BCG administration was considered the natural (gastrointestinal tract) route for acquiring TB in infants and children fed with unpasteurized milk. TB is poverty related with major burden in the poor and developing parts of the world. The incidence of TB is increasing worldwide due to poverty and inequity and is aggravated with the HIV/AIDS pandemic, which greatly increases risk of infection proceeding to active disease. Diabetes, metabolic syndrome, smoking and more recently vitamin deficiencies due to malnutrition and poor socioeconomic conditions are emerging as important risk factors for TB. Importantly, how these factors can influence efficacy evaluation of new TB vaccines requires specific attention when defining clinical trial designs that involve study or patient populations with a variety of such risk factors. Because of the rising globalization and emergence of multidrug-resistant (MDR) and extensively drug resistant TB (XDR) strains, TB is increasingly becoming a serious threat for the entire world.

Today TB has reached alarming proportions of 10.0 million incidence cases and 1.6 million deaths attributed to the disease as reported by the latest World Health Organization (WHO) global TB report 2018. Globally, some 50 million individuals are already latently infected with MDR *M tuberculosis* strains creating a remarkable resource for future cases of active TB with insufficient treatment options. Nevertheless, the WHO End TB Strategy has vowed to reduce TB morbidity by 90% and TB mortality by 95% by 2035 and recognizes the urgent need for more accessible diagnostic tools that are rapid and reliable, new less toxic and more efficacious antibiotics to shorten therapy and ultimately new vaccines to prevent pulmonary TB in order to achieve this ambitious goal.

The present invention contributes to the objective of providing new vaccines to prevent TB.

BRIEF DESCRIPTION OF THE INVENTION

The present invention refers to a live-attenuated *M. tuberculosis* vaccine composition, preferably a reconstituted composition after freeze-drying, comprising an isolated microorganism belonging to a MTBVAC strain having a i) PhoP-phenotype by the inactivation by a genetic deletion of the Rv0757 gene and ii) the deletion of a second gene, Rv2930 (fadD26), that prevents PDIM production (PDIM- phenotype), wherein said composition is characterized in that it comprises the following components per mL (in terms of percentages):

| Components | MTBVAC Dose per 1 mL |
|---|---|
| L-Asparagine | 0.034-0.066% |
| Monopotassium phosphate | 0.006-0.010% |
| Magnesium sulfate $H_2O$ | 0.008-0.012% |
| Ammonium ferric citrate | 0.0004-0.0008% |
| Dextrose monohydrate | 0.05-0.066% |
| Glycerol | 0.00005-0.0001% |
| Citric acid | 0.026-0.034% |
| Polysorbate 80 | 0.000002-0.000008% |
| Sodium glutamate | 0.33-1.33% |
| Sucrose | 3.3-13.3% |
| Purified water QS | 1 mL |

BRIEF DESCRIPTION OF THE FIGURES

Other objects, advantages and novel features of the present invention will become apparent from the following detailed description of the invention when considered in conjunction with the accompanying drawings.

but provides greater assurance of genetic stability. Light blue depicts the phoP gene, fadD26 gene is shown in light orange, antibiotic resistance cassettes km$^r$ and hyg$^r$ are in magenta, yellow triangles depict res sites flanking Ωhyg$^r$ or the residual res site in the deleted regions; res sites do not contain any exogenous coding sequence.

DETAILED DESCRIPTION OF THE INVENTION

Definitions and Detailed Description of the MTBVAC Strain

The "MTBVAC strain" will be used to refer to the isolated microorganism of the *M. tuberculosis* strain that has deleted the Rv0757 gene in *M. tuberculosis* MT103 clinical strain and which additionally comprises the deletion of the Rv2930 (fadD26) gene. Therefore, said strain presents two independent mutations derived from *M. tuberculosis*, the independent phoP deletion not affecting the properties of the vaccine derived from the inactivation of said gene. Therefore, "the MTBVAC strain" is characterized in that PDIM production is inactivated through the deletion of the Rv2930 (fadD26) gene, and thus this strain is characterized in that it comprises the deletion of the Rv2930 and Rv0757 genes.

It is thus noted that the MTBVAC strain was constructed to contain two independent non-reverting deletion mutations, without antibiotic markers, fulfilling the first Geneva consensus safety requirements for advancing live mycobacterial vaccines to phase I clinical evaluation. The MTBVAC strain was genetically engineered to phenotypically and functionally resemble its prototype SO2. SO2 is a marked Mt103 phoP mutant by the insertion of a kanamycin resistance cassette (kmr) (Mt103phoP::kmr) (see FIG. 11), which in addition to the engineered PhoP– deficient phenotype, SO2 has an acquired spontaneous loss in PDIM biosynthesis (see FIG. 2 of Dessislava Marinova, Jesus Gonzalo-Asensio, Nacho Aguilo & Carlos Martin (2017) MTBVAC from discovery to clinical trials in tuberculosis-endemic countries, Expert Review of Vaccines, 16:6, 565-576, DOI: 10.1080/14760584.2017.1324303), a process described to be common in *M. tuberculosis* as result of repeated laboratory subculture and manipulation practices.

Figure 11:
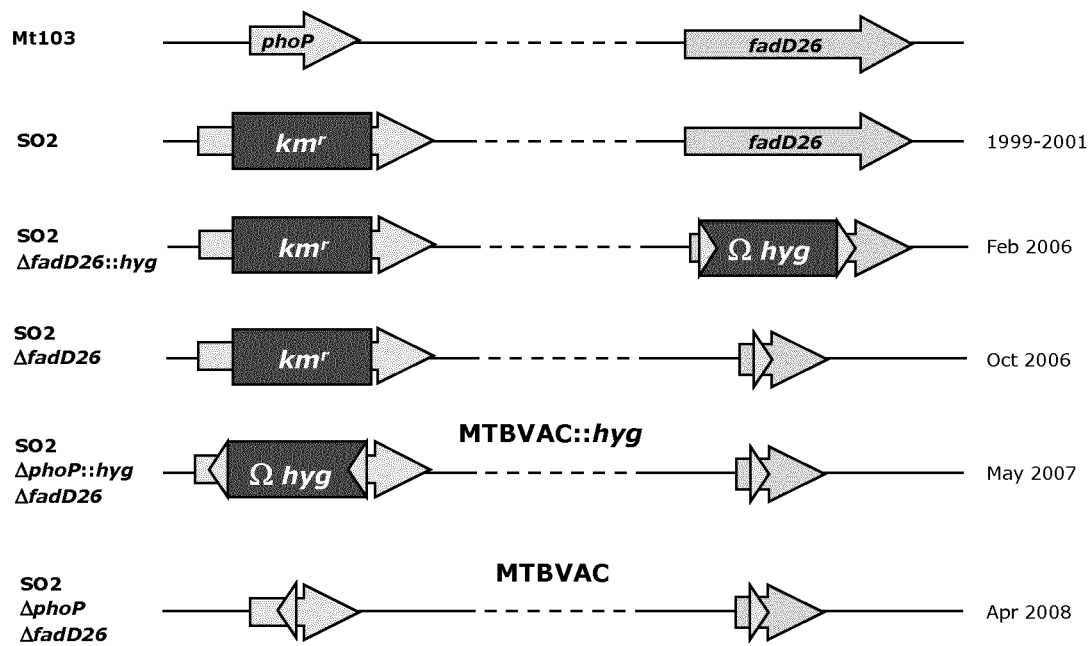
FIG. 11. Step-by-step construction from SO2 to MTB-VAC. The final double-deletion strain is phenotypically identical to prototype SO2 (phoP- based PDIM- deficient)

As reflected in FIG. 11, MTBVAC strain was constructed following a stepwise approach. First, the unmarked deletion in fadD26 was introduced in SO2, giving rise to SO2ΔfadD26. Consequently, the unmarked deletion in phoP in SO2ΔfadD26 generated the MTBVAC strain. For construction of MTBVAC, suicide plasmids harbouring the deleted fadD26 and phoP genes, whose deleted regions were interrupted with a hygromycin resistance marker (hyg$^r$) flanked by res sites on each side (res::hyg$^r$::res), were used. γδ-resolvase from *E. coli* catalyzed the excision of the antibiotic resistance cassette following recognition of the res sites, thereafter leaving a copy of a residual res "scar" in place of the deletion (Malaga, et al. 2003); res sites do not contain any exogenous coding sequence. The final construct SO2ΔfadD26::ΔphoP was named MTBVAC strain. In the MTBVAC strain, the introduction of an unmarked deletion in fadD26 ensures a genetically stable abolishment of PDIM biosynthesis. The size of the generated deletion in the gene fadD26 comprises 1,511 bp and results in complete inactivation of this essential gene in PDIM biosynthesis. The wild-type gene is 1,752 bp (583 amino acids). A residual res scar was left in the process of the excision of hyg$^r$ by γδ-resolvase. As a result of this deletion, the transcription levels of the next five genes in the PDIM locus (fadD26–ppsE) are diminished and PDIM biosynthesis in MTBVAC is completely abolished (Ainhoa Arbués PhD Thesis). The PDIM locus in *M. tuberculosis* comprises 13 genes clustered on a 50-kb fragment of the chromosome. The region is the biggest operon in the genome of *M. tuberculosis* (Camacho, et al. 2001; Camacho, et al. 1999; Cox, et al. 1999; Trivedi, et al. 2005).

In *M. tuberculosis*, phoP (744 bp) maps upstream of phoR (1458 bp) and both genes are transcribed in the same direction. Replacement of the generated 94-bp deletion within the phoP gene by the residual res site entails the presence of multiple STOP codons that on the other hand results in lack of translation of the DNA binding domain (equivalent to 92 amino acids) of PhoP in MTBVAC.

The deletions in phoP and fadD26 genes in MTBVAC can be detected/localised using a RT-PCR presence/absence approach. The method uses fluorescent-based PCR reagents (primers and probes) to indicate the presence of the res sites in ΔphoP and ΔfadD26 genes and absence of the wild-type phoP and fadD26 genes.

Herein below, we provide the open-reading frame (ORF) sequence of fadD26 gene in Mt103 a) and in MTBVAC (ΔfadD26) b); and the ORF sequence of phoP gene in Mt103 c) and in MTBVAC (ΔphoP) d). The nucleotide sequence corresponding to the deleted gene regions in fadD26 (a) and phoP (c) are depicted in small letters; residual res site is highlighted in grey. For the fluorescent-based PCR detection method, primers for each target are underlined and the Taq-man probe is shown in bold.

```
a) wild-type fadD26 gene in Mt103
                                                                  SEQ ID NO 1
ATGCCGGTGACCGACCGTTCAGTGCCCTCTTTGCTGCAAGAGAGGGCCGACCAGCAGCCTGACAGCACTGCATAT
ACGTACATCGACTACGGATCCgaccccaagggatttgctgacagcttgacttggtcgcaggtctacagtcgtgcatgcatcattgctgaagaa
ctcaagttatgcgggttaccggagatcgagtggcggttttagcgccacaaggactggaatatgtccttgcattcctgggcgcacttcaggctggattt
atcgcggttccgctgtcaactccacagtatggcattcacgatgaccgcgtttctgcggtgttgcaggattccaagccggtagccattctcacgacttcgt
ccgtggtaggcgatgtaacgaaatacgcagccagccacgacgggcagcctgccccggtcgtagttgaggttgatctgcttgatttggactcgccgcga
cagatgccggctttctctcgtcagcacaccggggcggcttatctccaatacacgtccggatcgacgcgtacgccggccggagtcattgtgtcgcacacg
aatgtcattgccaatgtgacacaaagtatgtacggctatttcggcgatcccgcaaagattccgaccgggactgtggtgtcgtggctgcctttgtatcacg
atatgggcctgattctcggaatttgcgcaccgctggtggcccgacgccgcgatgttgatgagcccaatgtcattttgcgccgtccggccgctggat
gcaactgcttgccaccagcggccggtgcttttctgcggcaccgaatttcgccttcgagctggccgtgcgcagaacatctgaccaggacatggcggggct
cgacctgcgcgacgtggtcggcatcgtcagtggcagtgagcgaatccatgtggcaacgtgcggcggttcatcgagcggttcgcgccgtacaatctca
gccccaccgcgatacggccgtcgtacgggctcgcggaagcgaccttatatgtggcagctcccgaagccggcgccgcgcccaagacggtccgtttgac
tacgagcagctgaccgccggcgaggctcggcctcggaaccgatgggtcggtcggcaccgaactgatcagctacggctccccccgacccatcgtctgt
gcgaatcgtcaaccccggagaccatggttgagaatccgcctggagtggtcggtgagatctgggtgcatggcgaccacgtgactatgggtattggcag
aagccgaagcagaccgcgcaggtcttcgacgccaagctggtcgatccgcgccggcagccccggaggggccgtggctgcgcaccggcgacctgggc
gtcatttccgatggtgagctgttcatcatgggccgcatcaaagacctgctcatcgtggacgggcgcaaccactacccgacgacatcgaggcaacgat
ccaggagatcaccggtggacgggccgcggcgatcgcagtgcccgacgacatcaccgaacaactggtggcgatcatcgaattcaagcgacgcggtag
taccgccgaagaggtcatgctcaagctccgctcggtgaagcgtgaggtcacctccgcGATATCGAAGTCACACAGCCTGCGGGTGGCC
GATCTCGTTCTGGTGTCACCTGGTTCGATTCCATCACCACCAGCGGCAAGATCGGCGGTCAGCCTGCGTCGAAC
GCTATCGCAGCGACGGCTTCAAGCGGCTGGACGTAGCCGTATGA.
```

-continued b) ΔfadD26 in MTBVAC

SEQ ID NO 2

ATGCCGGTGACCGACCGTTCAGTGCCCTCTTTGCTGCAAGAGAGGGCCGACCAGCAGCCTGACAGCACTGCATAT
ACGTACATCGACTACGGATCCACTAGTTCTAGAGCAACCGTCCGAAATATTATAAATTATCGCACACATAAAAACA
GTGCTGTTAATGTGTCTATTAAATCGATTTTTGTTATAACAGACACTGCTTGTCCGATATTTGATTTAGGATACATT
TTTATGAGATCCCCCGGGCTGCAGGAATTCGATATCGAAGTCACACAGCCTGCGGGTGGCCGATCTCGTTCTGGT
GTCACCTGGTTCGATTCCCATCACCACCAGCGGCAAGATCCGGCGGTCAGCCTGCGTCGAACGCTATCGCAGCGA
CGGCTTCAAGCGGCTGGACGTAGCCGTATGA.

c) wild-type phoP gene in Mtl03

SEQ ID NO 3

ATGCGGAAAGGGGTTGATCTCGTGACGGCGGGAACCCCAGGCGAAAACACCACACCGGAGGCTCGTGTCCTCGT
GGTCGATGATGAGGCCAACATCGTTGAACTGCTGTCGGTGAGCCTCAAGTTCCAGGGCTTTGAAGTCTACACCGC
GACCAACGGGGCACAGGCGCTGGATCGGGCCCGGGAAACCCGGCCGGACGCGGTGATCCTCGATGTGATGATGC
CCGGGATGGACGGCTTTGGGGTGCTGCGCCGGCTGCGCGCCGACGGCATCGATGCCCCGGCGTTGTTCCTGACG
GCCCGTGACTCGCTACAGGACAAGATCGCGGGTCTGACCCTGGGTGGTGACGACTATGTGACAAAGCCCTTCAGT
TTGGAGGAGGTCGTGGCCAGGCTGCGGGTCATCCTGCGACGCGCGGGCAAGGGCAACAAGGAACCACGTAATGT
TCGACTGACGTTCGCCGATatcgagctcgacgaggagacccacgaagtgtggaaggcgggccaaccggtgtcgctgtcgcccaccgaattc
accctgctgcgctatttcgtGATCAACGCGGGCACCGTGCTGAGCAAGCCTAAGATTCTCGACCACGTTTGGCGCTACGAC
TTCGGTGGTGATGTCAACGTCGTCGAGTCCTACGTGTCGTATCTGCGCCGCAAGATCGACACTGGGGAGAAGCGG
CTGCTGCACACGCTGCGCGGGGTGGGCTACGTACTGCGGGAGCCTCGATGA.

d) ΔphoP in MTBVAC

SEQ ID NO 4

ATGCGGAAAGGGGTTGATCTCGTGACGGCGGGAACCCCAGGCGAAAACACCACACCGGAGGCTCGTGTCCTCGT
GGTCGATGATGAGGCCAACATCGTTGAACTGCTGTCGGTGAGCCTCAAGTTCCAGGGCTTTGAAGTCTACACCGC
GACCAACGGGGCACAGGCGCTGGATCGGGCCCGGGAAACCCGGCCGGACGCGGTGATCCTCGATGTGATGATGC
CCGGGATGGACGGCTTTGGGGTGCTGCGCCGGCTGCGCGCCGACGGCATCGATGCCCCGGCGTTGTTCCTGACG
GCCCGTGACTCGCTACAGGACAAGATCGCGGGTCTGACCCTGGGTGGTGACGACTATGTGACAAAGCCCTTCAGT
TTGGAGGAGGTCGTGGCCAGGCTGCGGGTCATCCTGCGACGCGCGGGCAAGGGCAACAAGGAACCACGTAATGT
TCGACTGACGTTCGCCGATATCGAATTCCTGCAGCCCGGGGGATCTCATAAAAATGTATCCTAAATCAAATATCGG
ACAAGCAGTGTCTGTTATAACAAAAAATCGATTTAATAGACACATTAACAGCACTGTTTTTATGTGTGCGATAATTT
ATAATATTTCGGACGGTTGCTCTAGAACTAGTGGATCAACGCGGGCACCGTGCTGAGCAAGCCTAAGATTCTCGA
CCACGTTTGGCGCTACGACTTCGGTGGTGATGTCAACGTCGTCGAGTCCTACGTGTCGTATCTGCGCCGCAAGATC
GACACTGGGGAGAAGCGGCTGCTGCACACGCTGCGCGGGGTGGGCTACGTACTGCGGGAGCCTCGATGA.

SO2 has a thorough and complete preclinical history demonstrating robust safety and attenuation profile and promising efficacy compared to BCG in relevant animal models. Fortunately, most of these preclinical studies have been reproduced with MTBVAC to confirm functional profile and biological activity of the double attenuating PhoP− PDIM− phenotype. Lipid profile analyses have demonstrated that MTBVAC and its prototype SO2 are phenotypically comparable lacking DAT, PAT, and PDIM.

On the other hand, from hereinafter in the context of the present invention, BCG will be used to refer to the current vaccine that has been in use against tuberculosis since 1921. It is a live attenuated vaccine derived from a *M. bovis* strain that lost its virulence after being sub-cultured in the laboratory and which we now know has more than one hundred deleted genes. Behr, M. A. BCG—different strains, different vaccines *Lancet Infect Dis* 2002, 2(2), 86-92.

From hereinafter in the context of the present invention, H37Rv will be used to refer to a pathogenic *M. tuberculosis* strain that has been sequenced, Cole et al. referring to these genes as Rv (Ref Cole et al 1998 Deciphering the biology of *M. tuberculosis* from the complete genome sequence. *Nature* 393: 537-544).

From hereinafter in the context of the present invention MT103 will be used to refer to a *M tuberculosis* clinical isolate. Camacho et al. 1999 Identification of a virulence gene cluster of *M tuberculosis* by signature-tagged transposon mutagenesis. *Mol Microbiol* 34: 257-267.

From hereinafter in the context of the present invention PDIM− strain will be used to refer to the strain of the *M. tuberculosis* complex that is not capable of synthesizing phthiocerol dimycocerosates, which are important lipids related to the pathogenicity of *M. tuberculosis.*

From hereinafter in the context of the present invention SO2+pSO5 will be used to refer to the *M. tuberculosis* SO2 strain in which the mutation in Rv0757 is complemented by the Rv0757 gene by transformation of a replicative plasmid with the mycobacterial phoP gene, but it is not capable of complementing PDIM synthesis, its phenotype being PhoP+ PDIM−.

From hereinafter in the context of the present invention *M. tuberculosis* phoP− will be used to refer to the *M. tuberculosis* strain that has been inactivated by the Rv0757 gene deletion between the EcoRV-BspEI sites, its phenotype being phoP− PDIM+.

From hereinafter in the context of the present invention Rv2930 (fadD26) will be used to refer to the gene that is at the beginning of the operon that is responsible for the synthesis of phthiocerol dimycocerosates (PDIM) (Camacho et al.) and the elimination of this gene in *M. tuberculosis* confers a stable PDIM− phenotype.

DESCRIPTION

The use of vaccines to prevent TB in humans has proven to be a tremendous challenge for almost a century now. BCG, derived from *M. bovis*, is currently the only licensed TB vaccine in use and is the most widely used vaccine in the world. The development and generalized administration of the BCG vaccine since the beginning of the 1920s represented a significant advance, with the prospect of being able to eradicate TB from the world. However, these initial promises were not achieved and, from the results of a large number of efficacy trials, it is clear that the BCG vaccine in its current form is of limited use in controlling the disease, particularly in respiratory forms in adults in third world areas where the disease is endemic. Fine, P. E. Variation in protection by BCG: implications of and for heterologous immunity. *Lancet* 1995, 346(8986), 1339-1345. With more knowledge of the virulence of *M. tuberculosis* and immune response models that lead to the generation of protective immunity, it is possible to develop better vaccines than BCG. The observation that higher protection levels are achieved when the host is vaccinated with BCG suggests that viability and persistence are fundamental properties required for the success of a tuberculosis vaccine. In this sense, in U.S. Pat. No. 8,287,886 B2 it was taught that the use a *M. tuberculosis* strain with the inactivated Rv0757 (phoP) gene and a second independent mutation of phoP, which prevents PDIM synthesis, provided for a prototype single dose live vaccine, which was more attenuated than BCG in immunocompromised SCID mice, provided protection levels comparable to those conferred by BCG in mice and higher protection than BCG in guinea pigs.

The phoP gene, together with phoR, forms part of a two-component system that shows a high degree of similarity to other two-component systems that control the transcription of key virulence genes in intracellular pathogens. It also controls the expression of many other genes that are not directly involved in virulence. Groisman, E. A. The pleiotropic two-component regulatory system PhoP–PhoQ. *J Bacteriol* 2001, 183(6), 1835-1842. The elimination of virulence genes does not seem to be, per se, the only method for the attenuation of *M. tuberculosis*. It was shown that a pantothenate auxotrophic mutant of *M. tuberculosis*, which is incapable of de novo synthesis of pantothenic acid, persisted in SCID mice, without managing to cause the disease. Sambandamurthy, V. K., Wang, X., Chen, B. et al. A pantothenate auxotroph of *M. tuberculosis* is highly attenuated and protects mice against tuberculosis. *Nat Med* 2002, 8(10), 1171-1174. Individual leucine auxotrophs are also strongly attenuated and incapable of replication in vivo in SCID mice. Hondalus, M. K., Bardarov, S., Russell, R., Chan, J., Jacobs, W. R., Jr. & Bloom, B. R. Attenuation of and protection induced by a leucine auxotroph of *M. tuberculosis*. *Infect Immun* 2000, 68(5), 2888-2898. Therefore, the principle that vaccine strains based on *M. tuberculosis* can be successfully attenuated whilst retaining genes that are suppressed in *M. bovis* BCG is now generally accepted.

Prior to U.S. Pat. No. 8,287,886B2, research into more effective vaccines than BCG was based on the notion that loss of virulence with BCG was in itself a factor that contributed to its lack of complete protective efficacy. Behr, M. A., Wilson, M. A., Gill, W. P. et al. Comparative genomics of BCG vaccines by whole-genome DNA microarray. *Science* 1999, 284(5419), 1520-1523. It was therefore reasoned that new attenuated mutants of *M. tuberculosis*, with less virulence, could be more effective as vaccines. In this regard, and although it has been indicated that natural infection with *M. tuberculosis* and vaccination with BCG do not differ in their capacity to bring about protective immunity against tuberculosis. Sampson, S. L., Dascher, C. C., Sambandamurthy, V. K. et al. Protection elicited by a double leucine and pantothenate auxotroph of *M. tuberculosis* in guinea pigs. *Infect Immun* 2004, 72(5), 3031-3037, *M. tuberculosis* infected individuals with latent tuberculosis have a 79% lower risk of progressive tuberculosis after re-infection as compared to uninfected individuals (Andrews 2012. CID 54:784-790). In addition, and taking into account the fact, that most of these individuals might have been vaccinated with BCG, this is indicative that, in practice, there might be a difference in the protective immunity provided by BCG and by *M tuberculosis*. This raised questions as to whether or not it was possible to improve BCG by rational attenuation of *M. tuberculosis*. Within this context, the observation that the mutant *M. tuberculosis* strain described in U.S. Pat. No. 8,287,886 B2 with the combination of 2 independent mutations, in synthesis of the PhoP protein and in PDIM synthesis, is more attenuated than BCG in the SCID mouse model, even when applied at a dose 10 times higher than that of BCG, and the greater degree of protection than BCG in the guinea pig model, was deemed of particular relevance.

The mutant *M. tuberculosis* strain described in U.S. Pat. No. 8,287,886 B2 was characterized by being an isolated microorganism belonging to the *Mycobacterium* genus, comprising the inactivation of the Rv 0757 (phoP) gene and the inactivation of a second gene that prevented PDIM (phthiocerol dimycocerosates) production. In particular, such mutant *M. tuberculosis* strain described in U.S. Pat. No. 8,287,886B2 (the SO2 strain) was characterized in that it comprised the inactivation of the Rv 0757 (phoP) gene and a second independent mutation of phoP that prevented PDIM production.

It is interesting to note that, as described in U.S. Pat. No. 8,287,886B2, the SO2 strain was not deemed toxic in six guinea pigs that were inoculated with 50 times the vaccine dose in this species. In addition, their survival rate and weight curve was studied. The survival rate was 100% after the 6-month duration of the experiment. FIG. 12 of U.S. Pat. No. 8,287,886B2 shows the observed weight gain in all the animals over the 6 months, showing the non-toxicity of the SO2 strain (Y=weight in grams and X=time in weeks of infection). In addition, survival rate of vaccinated guinea pigs after infection with *M. tuberculosis* was also studied in U.S. Pat. No. 8,287,886B2 (FIG. 13). The protection study in guinea pigs tracked the survival rate of guinea pigs after 300 days. The survival rate curve was measured for unvaccinated guinea pigs (saline) and those vaccinated with the current BCG vaccine, with a *M. tuberculosis* phoP– strain or with the SO2 strain (phoP– and PDIM– mutant). After subcutaneous vaccination, the animals were infected with a virulent strain of *M. tuberculosis* (H37Rv) at a high dose to study the survival rate. After 60 days, the 6 guinea pigs that had not been vaccinated (saline) had died, whilst the groups vaccinated with the SO2 strain, phoP– and BCG had survived. After 300 days of infection 3 guinea pigs vaccinated with BCG and phoP– had died, compared to only one of the groups vaccinated with the SO2 strain, which indicates that the protection of the phoP mutant is similar to that of the current vaccine BCG, whereas vaccination with the SO2 strain, the phoP– and PDIM– double mutant, protected better in the guinea pig model. Furthermore, FIG. 14 of U.S. Pat. No. 8,287,886B2 shows the survival after 400 days of the guinea pigs tracked in FIG. 13. The 6 unvaccinated guinea pigs had died after 60 days. After 400 days of infection 3 guinea pigs from the group vaccinated with the SO2 strain (FIG. 14 *a*) survived, whereas just 1 guinea pig vaccinated with BCG (FIG. 14 *a* and FIG. 14 *b*) and phoP– (FIG. 14 *b*) had survived, indicating again that the protection of the phoP mutant is similar to that of BCG, whilst vaccination with the SO2 strain, the phoP– and PDIM– double mutant, protects better after the 400 days of the experiment.

In conclusion, the results described in U.S. Pat. No. 8,287,886B2 show that the SO2 strain and therefore a microorganism belonging to the *Mycobacterium* genus (particularly from the *M. tuberculosis* complex) with PhoP– PDIM– phenotype is a more effective vaccine than BCG in accordance with a number of criteria. It is more attenuated than BCG in SCID mice, it provides mice with a protective immunity that is at least as good as BCG and it generates stronger cellular immune responses. Additionally, in protection experiments conducted in guinea pigs against infection with high doses of H37Rv, the strain with phenotype PDIM– PhoP– results in a 100% survival rate of guinea pigs in circumstances in which BCG only achieved a 33% survival rate. This protection is linked to a reduction in the severity of the disease and the bacterial load.

In light of these results, the authors of the present invention proceeded to develop a live-attenuated *M. tuberculosis* vaccine comprising the MTBVAC strain presented as a lyophilised pellet in amber-glass vials of 3 mL. As already indicated, the MTBVAC strain was constructed to contain two independent non-reverting deletion mutations, without antibiotic markers, fulfilling the first Geneva consensus safety requirements. In this sense, the MTBVAC strain was genetically engineered to phenotypically and functionally resemble its prototype SO2. In the MTBVAC strain, the introduction of an unmarked deletion in fadD26 ensures a genetically stable abolishment of PDIM biosynthesis. It is noted that SO2 has a thorough and complete preclinical history demonstrating robust safety and attenuation profile and promising efficacy compared to BCG in relevant animal models. As already indicated, most of these preclinical studies have been reproduced with MTBVAC to confirm functional profile and biological activity of the double attenuating PhoP–/PDIM– deficient phenotype.

On the basis of the above, the authors of the present invention prepared a vaccine comprising the MTBVAC strain. One dose of 0.05 mL of said vaccine was to be given by using the intradermal route to newborns similarly to BCG. A first objective of the authors of the present invention was thus to obtain a, preferably lyophilized, vaccine useful in neonates for the treatment or prevention of TB in this specific age group population. With that in mind, they conducted, in neonates, the experiments described in examples 2 and 3 of the present application, wherein as a result of these experiments, it was concluded that vaccination with MTBVAC at the estimated dosages of $2.5 \times 10^4$ or $2.5 \times 10^5$ or more CFUs, was immunogenic in neonates from a TB endemic setting.

It is noted that in the present application, the term "neonates" is understood as a newborn child (or other mammal) or as an infant less than four weeks old.

In virtue of the above results, we are currently undertaking a Phase 2a Randomised Controlled Dose-defining Trial of the Safety and Immunogenicity of MTBVAC in healthy, BCG naïve, HIV unexposed, South African newborns. This study will be performed in a population of ninety-nine HIV unexposed, BCG naïve newborns without known household exposure to *M. tuberculosis*. The estimated study duration (first participant vaccinated to completion of data collection) will be approximately 36 months. In this study, MTBVAC will be administered to the neonates at three dose levels: $1.5-8.5 \times 10^4$ CFU/0.05 ml, $1.5-8.5 \times 10^5$ CFU/0.05 ml and $1.5-8.5 \times 10^6$ CFU/0.05 ml. The active control is the BCG vaccine. Participants will receive a single dose of MTBVAC or BCG administered intradermally on Study Day 0. The objectives of this study are as follows:

Primary:
To evaluate safety and reactogenicity of MTBVAC at escalating dose levels compared to BCG vaccine in healthy, BCG naïve, HIV unexposed, South African newborns.
To evaluate the immunogenicity of MTBVAC at escalating dose levels in healthy, BCG naïve, HIV unexposed, South African newborns.

Secondary:
To evaluate QuantiFERON-TB Gold Plus (QFT) conversion rate in neonates receiving escalating dose levels of MTBVAC.

Exploratory:
To evaluate differences in major histocompatibility (MHC)-restricted T-cell responses induced by MTBVAC and BCG vaccination.
To evaluate differences in donor-unrestricted T-cell responses induced by MTBVAC and BCG vaccination.

Taking into account the fact that examples 2 and 3 already indicate that vaccination with MTBVAC at the estimated dosages of $2.5 \times 10^4$ or $2.5 \times 10^5$ or more CFUs were immunogenic in neonates from a TB endemic setting, and that the reactogenicity of the MTBVAC vaccine was clearly lower than the reactogenicity produced with the BCG vaccine, it appears plausible that administration of MTBVAC to neonates at doses of $1.5-8.5 \times 10^4$ CFU/0.05 ml, $1.5-8.5 \times 10^5$ CFU/0.05 ml or $1.5-8.5 \times 10^6$ CFU/0.05 ml, would be useful as a prophylactic agent to neonates at risk of infection with *M. tuberculosis* or those at risk of developing tuberculosis disease.

Therefore, in a first aspect, the invention refers to a composition comprising an isolated microorganism belonging to the *M. tuberculosis* complex, preferably a *M. tuberculosis* clinical isolate, more preferably a *M. tuberculosis* clinical isolate, characterized in that it comprises a PhoP– phenotype by the inactivation by a genetic deletion of the Rv0757 gene and the deletion of a second gene, Rv2930 (fadD26), that prevents PDIM production (PDIM– phenotype), more preferably said microorganism is the MTBVAC strain, wherein the composition comprises at least $1.5 \times 10^4$ cfu/0.05 ml or more of the isolated microorganisms. Preferably, the composition comprises between $1.5 \times 10^4$ cfu/0.05 ml and $8.5 \times 10^6$ cfu/0.05 ml isolated microorganisms. More preferably, the composition comprises between $1.5-8.5 \times 10^4$ cfu/0.05 ml, or between $1.5-8.5 \times 10^5$ cfu/0.05 ml or between $1.5-8.5 \times 10^6$ cfu/0.05 ml of the isolated microorganisms.

In a second aspect of the invention, the composition of the first aspect is administered for prophylaxis in neonates at risk of infection with *M. tuberculosis* or those at risk of developing tuberculosis disease, against infections caused by *M. tuberculosis* complex, preferably *M. tuberculosis*; or for use in the prophylaxis or prevention in neonate humans at risk of developing tuberculosis disease and suffering from latent tuberculosis infection, against the development of the clinical symptomatology associated with the active form of the disease caused by *M. tuberculosis* complex, preferably *M. tuberculosis*; or for use as a secondary agent for treating patients infected with latent and/or active TB tuberculosis in neonates; or for use in revaccination, booster vaccination or booster dose in a prophylactic or preventive treatment in neonate humans at risk of infection with *M. tuberculosis*, against infections caused by *M. tuberculosis* complex, preferably *M. tuberculosis*; or for use as a secondary agent for prevention of any unrelated infections other than tuberculosis disease caused by *M. tuberculosis*, including infection by non-tuberculous mycobacteria in neonates. More preferably, said composition is administered via the intradermal route to the neonates.

In addition to the above, it is further noted that we are currently conducting a double-blind, randomized, BCG-controlled, dose-escalation safety and immunogenicity study in adults with and without latent tuberculosis infection (LTBI), as measured by QuantiFERON-TB Gold Plus (QFT) assay. This is a Phase 1b/2a, double-blind, randomized, BCG-controlled, dose-escalation safety and immunogenicity study in healthy adults with and without LTBI. All participants will have received previous BCG vaccination in infancy. The investigational product is MTBVAC at four dose levels: $5 \times 10^3$ CFU, $5 \times 10^4$ CFU, $5 \times 10^5$ CFU, and $5 \times 10^6$ CFU. The active control is BCG ($5 \times 10^5$ CFU).

Participants meeting the inclusion/exclusion criteria will be randomized within a study cohort to receive a single dose of MTBVAC or BCG revaccination administered intradermally on Study Day 0. The study will be conducted at one site in South Africa. Participants will be enrolled into one of eight cohorts and followed for safety and immunogenicity endpoints through Study Day 182. The estimated time to complete enrolment is approximately 9 months.

Cohorts 1-8 will include QFT-negative (Cohorts 1-4) and QFT-positive (Cohorts 5-8) participants. Participants will be randomized within each cohort, to receive either MTBVAC or BCG.

On these bases, in a third aspect, the invention refers to a composition comprising an isolated microorganism belonging to the *M. tuberculosis* complex, preferably a *M. tuberculosis* clinical isolate, more preferably *M. tuberculosis* clinical isolate MT103, characterized in that it comprises a PhoP− phenotype by the inactivation by a genetic deletion of the Rv0757 gene and the deletion of a second gene, Rv2930 (fadD26), that prevents PDIM production (PDIM− phenotype), more preferably said microorganism is the MTBVAC strain, wherein the composition comprises at least $3\times10^3$ cfu/0.1 ml or more of the isolated microorganisms. Preferably, the composition comprises between $3\times10^3$ CFUs/0.1 ml and $17\times10^6$ cfu/0.1 ml of isolated microorganisms. More preferably, the composition comprises between $3\text{-}17\times10^3$ cfu/0.1 ml, or between $3\text{-}17\times10^4$ cfu/0.1 ml, or between $3\text{-}17\times10^5$ cfu/0.1 ml or between $3\text{-}17\times10^6$ cfu/0.1 ml of the isolated microorganisms.

In a fourth aspect of the invention, the composition of the third aspect is administered for prophylaxis or prevention (including booster vaccination) in non-neonate humans, such as children, adolescents and adults at risk of infection with *M. tuberculosis*, against infections caused by *M. tuberculosis* complex, preferably *M. tuberculosis*. More preferably, said composition is administered via the intradermal route.

In a fifth aspect of the invention, the composition of the third aspect is administered for prophylaxis or prevention in non-neonate humans, such as children, adolescents and adults at risk of developing tuberculosis disease and suffering from latent tuberculosis infection, against the development of the clinical symptomatology associated with the active form of the disease caused by *M tuberculosis* complex, preferably *M. tuberculosis*. More preferably, said composition is administered via the intradermal route.

In a sixth aspect of the invention, the composition of the third aspect is administered for use as a secondary agent for treating patients infected with latent and/or active TB in neonates and non-neonate humans, such as children, adolescents and adults. More preferably, said composition is administered via the intradermal route.

In a seventh aspect of the invention, the composition of the third aspect is administered for booster vaccination or booster dose in a prophylactic or preventive treatment in non-neonate humans, such as children, adolescents and adults at risk of infection with *M. tuberculosis*, against infections caused by *M. tuberculosis* complex, preferably *M. tuberculosis*. In this sense, it is noted that after initial immunization, a booster injection or booster dose is a re-exposure to the immunizing antigen. It is intended to increase immunity against that antigen back to protective levels, after memory against that antigen has declined through time.

On the other hand, the authors of the present invention, in order to achieve a preferred manner of practicing any of the above mentioned aspects of the invention with the MTBVAC strain and of minimizing the loss of viability after lyophilization in a development process that offers consistent results and a product with a shelf life of at least 2 years stored between +2-8° C., carried out numerous studies to establish the most appropriate production process for the MTBVAC vaccine. As a first approximation, different culture media as well as different stabilizer compositions were tested.

The first challenge in the production of the MTBVAC vaccine was to cultivate it in a medium with a defined composition and in which there were no components of animal origin. For this reason, experiments were performed by using the SO2 strain. It is noted, as already mentioned, that the MTBVAC strain was genetically engineered to phenotypically and functionally resemble its prototype SO2, and therefore, the SO2 strain was considered an appropriate starting point to establish the most appropriate production process for the MTBVAC vaccine.

By using the SO2 strain, different media were developed and tested that did not contain any component of animal origin in its composition. Some of the proven culture media were as follows:

Middlebrook 7H9 and variations (Media for Tubercle Bacilli, Dubos, R. J. and Middlebrook, G. American Review of Tuberculosis and Pulmonary Diseases, 1947 Vol. 56 No. 4 pp. 334-45 ref 15).

Sauton synthetic medium (Handbook of Microbiological Media, Fourth Edition, Ronald M. Atlas, CRC Press, 2010. Page 1540) and variations.

The composition of the Sauton and Middlebrook media are detailed in the following tables:

TABLE 1

| Sauton | |
|---|---|
| Glycerol | 2% |
| L-Asparagine | 0.4% |
| Glucose | 0.2% |
| Citric acid | 0.2% |
| Monopotassium phosphate | 0.05% |
| Magnesium sulphate | 0.055% |
| Polysorbate 80 | 0.0155% |
| Ammonium ferric citrate | 0.005% |
| Zinc sulfate | 0.00001% |

TABLE 2

| Middlebrook 7H9 + ADC + Polysorbate | |
|---|---|
| Disodium phosphate | 2.5 g/L |
| Monopotassium phosphate | 1.0 g/L |
| Glutamic acid | 0.5 g/L |
| Ammonium sulfate | 0.5 g/L |
| Sodium citrate | 0.1 g/L |
| Magnesium sulphate | 50.0 mg/L |
| Ammonium ferric citrate | 40.0 mg/L |
| Zinc sulfate | 1.0 mg/L |
| Copper sulphate | 1.0 mg/L |
| Pyridoxine | 1.0 mg/L |
| Calcium chloride | 0.5 mg/L |
| Biotin | 0.5 mg/L |
| Glycerol | 2.0 mL/L |
| Bovine albumin | 5.0 g/L |
| Dextrose | 2.0 g/L |
| Catalase | 3.0 mg/L |
| Polysorbate 80 | 0.5 g/L |

In the Sauton media the growth was similar to the reference medium (Middlebrook medium without modifications, Table 2). FIG. 1 compares the growth curve in Middlebrook with that of the Sauton culture medium. In parallel to the composition of the culture medium, in these tests it began to profile at laboratory scale other variables such as the time of culture, the number of passages of culture and the type of growth, static or in agitation (see Table 3)

TABLE 3

Growth of M tuberculosis SO2 in Sauton Medium
Growth of M. tuberculosis SO2 in Sauton Medium

| Culture conditions |

TABLE 5-continued

Lyophilization of SO2 with different stabilizers.

| Batch | Specification | GSA | G | GSM | M | MS | GSB | GC | GS | CGS | CFT | GT | S |
|---|---|---|---|---|---|---|---|---|---|---|---|---|---|
| 009 | % loss lyophilization | 31% | | 20% | 77% | | | | | | | | |
| | % loss at 37° C. | 85% | | >99% | >99% | | | | | | | | |
| 010 | % loss lyophilization | 70% | | | 91% | | 54% | 79% | | | | | |
| | % loss at 37° C. | 88.5% | | | >99% | | >99% | >99% | | | | | |
| 011 | % loss lyophilization | 9.40% | | | | | | | | 61% | | | |
| | % loss at 37° C. | 57% | | | | | | | | >99% | | | |
| 012 | % loss lyophilization | 84% | | | | | 97% | | | 95% | 98% | >99% | |
| | % loss at 37° C. | >99% | | | | | >99% | | | >99% | >99% | >99% | |

After the above mentioned preliminary trials, it was concluded that it was necessary to add a stabilizer to the culture medium to lyophilize, since the losses in lyophilization without stabilizer were greater than 99%, and the best stabilizer to meet the specification for lyophilization loss and the specification for accelerated stability at 37° C., was GSA (Sodium glutamate and Sucrose).

After reaching the above conclusions, the MTBVAC strain was received in the form of a freeze-dried Pre-master seed lot, and shortly after, we began the cell cultures of this particular strain. For the growth of the MTBVAC strain, first Sauton media with the same composition as that used in the growth studies of the parental strain SO2 (see table 1) was used. However, unexpectedly, in the case of MTBVAC, a lower growth was observed in Sauton synthetic medium than that observed for the SO2 strain. In addition, problems in the amplification phase of the MTBVAC strain were also detected. In order to solve these problems, tests were performed adding and eliminating components from the Sauton media composition. Such modifications consisted on the addition or elimination of supplements such as glucose, zinc sulphate, biotin, glycerol and polysorbate.

The enrichment of the Sauton synthetic medium with zinc sulfate and biotin did not offer good results and no growth of MTBVAC was observed. In the case of enrichment with glucose, polysorbate and glycerin, the results were favorable and an adequate growth of MTBVAC was obtained.

Figure 1:
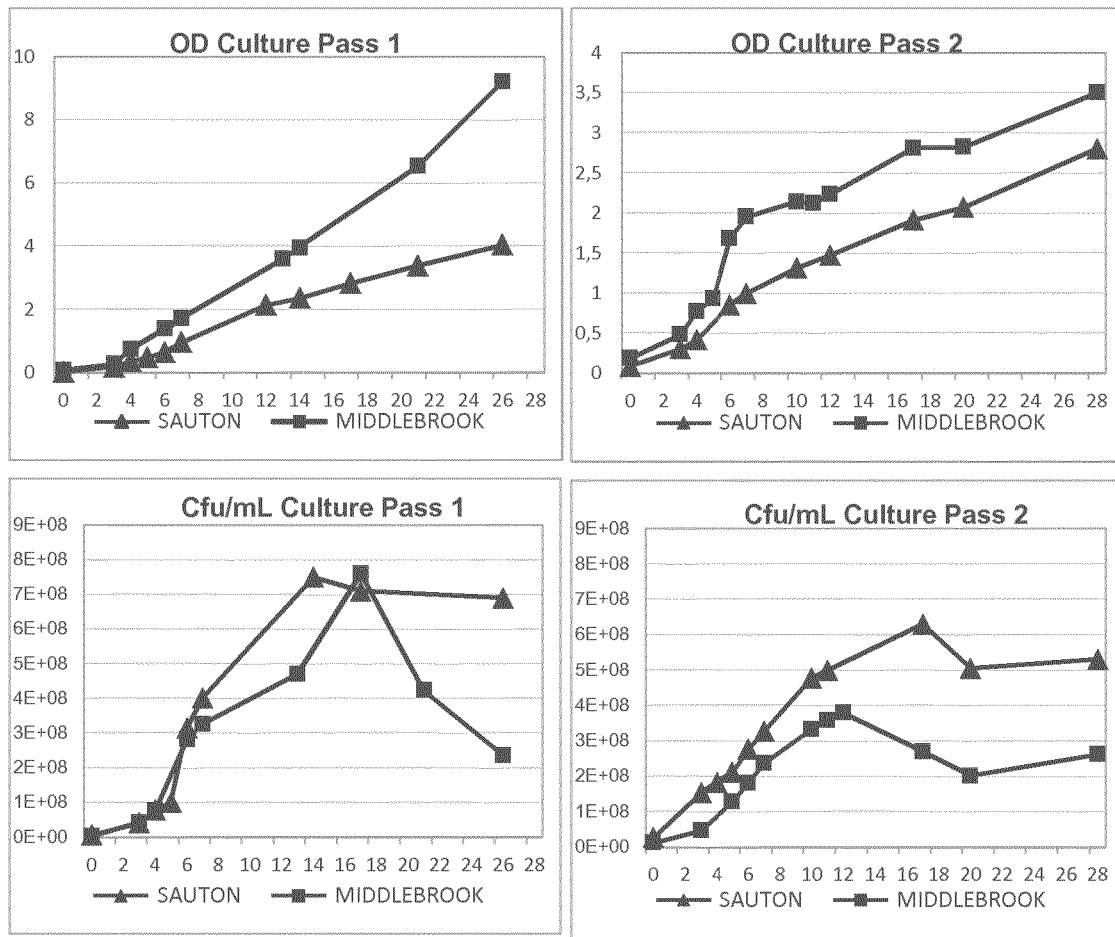
FIG. 1. Growth of the SO2 strain in Middlebrook 7H9 medium and synthetic Sauton medium. Results of OD and Cfu/mL of culture passes 1 and 2.
Figure 2:
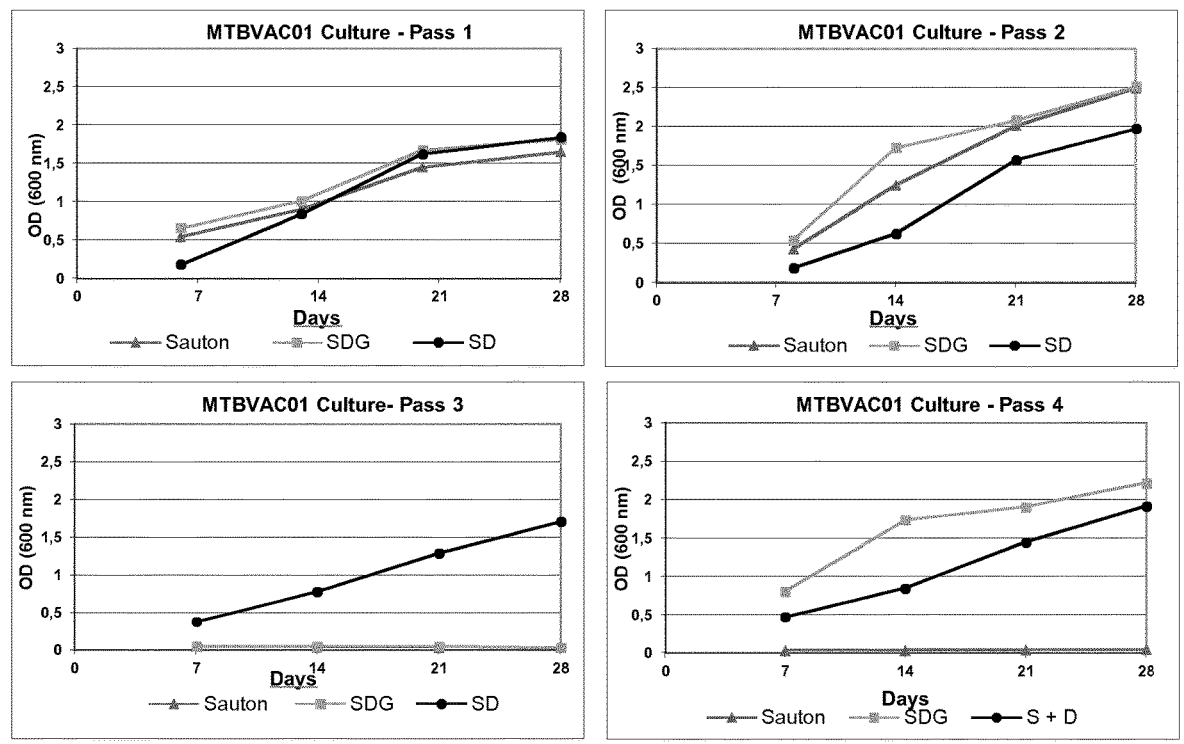
FIG. 2 shows the OD results of the MTBVAC cultures in Sauton, SD and SDG media.

As a result of these growth studies SD and SDG media were developed and the MTBVAC cultures were grown in these media. The growth of MTBVAC was good both in SD medium and in SDG medium, but some cultures were stopped after successive passages in SDG medium, so the SD medium was the one selected for the amplification passages. FIG. 2 shows the OD results of the MTBVAC cultures in Sauton, SD and SDG media.

However, when cultures of the MTBVAC strain were initiated from vials of the lyophilized or freezed-dried Master seed lot, it was observed that the growth could not be initiated in the SD medium, so modifications were made in the composition thereof and a seed medium was developed. As a conclusion of these studies and for future pilot and industrial tests as a means to start the cultures, the seed medium was selected, as a means for the amplification passages the SD medium was selected, and as a means for the mass culture before lyophilization, the SDG medium was selected. In addition, it is important to note that the composition of the SD medium in combination with the stabilizer affected the lyophilization process and the appearance of the tablet, therefore the lyophilization process will only be performed in the SDG medium.

We herein provide the composition of the Seed, SD and SDG media.

TABLE 6

| Components | Seed medium | SD medium | SDG medium |
|---|---|---|---|
| L-Asparagine | 2.00-4.00 g | 2.00-4.00 g | 2.00-4.00 g |
| Monopotassium phosphate | 0.30-0.60 g | 0.30-0.60 g | 0.30-0.60 g |
| Magnesium sulfate $H_2O$ | 0.5-0.70 g | 0.50-0.70 g | 0.50-0.70 g |
| Ammonium ferric citrate | 0.02-0.05 g | 0.02-0.05 g | 0.02-0.05 g |
| Dextrose monohydrate | 7.00-8.00 g | 3.00-4.00 g | 3.00-4.00 g |
| Glycerol | 10.0-20.0 mL | 30-40 mL | 3.0-10.0 mL |
| Citric acid | 1.5-2.0 g | 1.5-2 g | 1.5-2 g |
| Polysorbate 80 | | 0.15-0.5 mL | 0.15-0.5 mL |
| Purified water QS | 1.00 L | 1.00 L | 1.00 L |

In this sense, the following three tables show the results of the industrial scale production of five batches of MTBVAC $2.5 \times 10^5$ that demonstrate the consistency of the results obtained with the means developed in the study.

TABLE 7

| Culture of MTBVAC from the lyophilized working seed-bank in seed medium | | | | | |
|---|---|---|---|---|---|
| | Control | Lot 170928 | Lot 170580 | Lot 171811 | Lot 171911 | Lot 172547 |
| Culture appearance | | conformable | conformable | conformable | conformable | conformable |
| Purity (EP 2.6.1) | | Absence of contamination | Absence of contamination | Absence of contamination | Absence of contamination | Absence of contamination |

TABLE 7-continued

Culture of MTBVAC from the lyophilized working seed-bank in seed medium

| Control | Lot 170928 | Lot 170580 | Lot 171811 | Lot 171911 | Lot 172547 |
|---|---|---|---|---|---|
| Purity (Ziehl-Neelsen) | Acid-alcohol resistant *bacilli* | Acid-alcohol resistant *bacilli* | Acid-alcohol resistant *bacilli* | Acid-alcohol resistant *bacilli* | Acid-alcohol resistant *bacilli* |
| Viable bacteria count | $1.37 \times 10^6$ cfu/mL | $5.3 \times 10^6$ cfu/mL | $5.4 \times 10^6$ cfu/mL | $7.5 \times 10^6$ cfu/mL | $1 \times 10^6$ cfu/mL |

TABLE 8

Culture of MTBVAC in SD medium from the previous passage (Table 7)

| Control | Lot 170928 | Lot 170580 | Lot 171811 | Lot 171911 | Lot 172547 |
|---|---|---|---|---|---|
| Culture Appearance | conformable | conformable | conformable | conformable | conformable |
| Purity (EP 2.6.1) | Absence of contamination | Absence of contamination | Absence of contamination | Absence of contamination | Absence of contamination |
| Purity (Ziehl-Neelsen) | Acid-alcohol resistant *bacilli* | Acid-alcohol resistant *bacilli* | Acid-alcohol resistant *bacilli* | Acid-alcohol resistant *bacilli* | Acid-alcohol resistant *bacilli* |
| Viable bacteria count | $6.04 \times 10^8$ cfu/mL | $4.33 \times 10^8$ cfu/mL | $1.16 \times 10^8$ cfu/mL | $3.16 \times 10^8$ cfu/mL | $3.26 \times 10^8$ cfu/mL |

TABLE 9

Culture of MTBVAC in SD medium from the previous passage (Table 8)

| Control | Lot 170928 | Lot 170580 | Lot 171811 | Lot 171911 | Lot 172547 |
|---|---|---|---|---|---|
| Culture Appearance | conformable | conformable | conformable | conformable | conformable |
| Purity (EP 2.6.1) | Absence of contamination | Absence of contamination | Absence of contamination | Absence of contamination | Absence of contamination |
| Purity (Ziehl-Neelsen) | Acid-alcohol resistant *bacilli* | Acid-alcohol resistant *bacilli* | Acid-alcohol resistant *bacilli* | Acid-alcohol resistant *bacilli* | Acid-alcohol resistant *bacilli* |
| Viable bacteria count | $1.73 \times 10^8$ cfu/mL | $3.03 \times 10^8$ cfu/mL | $3.02 \times 10^8$ cfu/mL | $1.27 \times 10^8$ cfu/mL | $3.7 \times 10^8$ cfu/mL |

TABLE 10

Culture of MTBVAC in SDG medium from the previous passage (Table 9)

| Control | Lot 170928 | Lot 170580 | Lot 171811 | Lot 171911 | Lot 172547 |
|---|---|---|---|---|---|
| Culture Appearance | conformable | conformable | conformable | conformable | conformable |
| Purity (EP 2.6.1) | Absence of contamination | Absence of contamination | Absence of contamination | Absence of contamination | Absence of contamination |
| Purity (Ziehl-Neelsen) | Acid-alcohol resistant *bacilli* | Acid-alcohol resistant *bacilli* | Acid-alcohol resistant *bacilli* | Acid-alcohol resistant *bacilli* | Acid-alcohol resistant *bacilli* |
| Viable bacteria count | $7.1 \times 10^8$ cfu/mL | $4.33 \times 10^8$ cfu/mL | $4.51 \times 10^8$ cfu/mL | $2.77 \times 10^8$ cfu/mL | $3.26 \times 10^8$ cfu/mL |

In the previous indicated studies of development with the SO2 strain, we concluded that in the lyophilization process it was necessary to use a stabilizer to reduce the losses of viable bacteria count and to improve the stability of the lyophilized product. For the development of MTBVAC, the same stabilizers selected in the study with SO2 were used. The objective was to obtain a lyophilized vaccine with a concentration ranging from $3 \times 10^3$ cfu/0.1 ml and $17 \times 10^6$ cfu/0.1 ml, preferably ranging from $3-17 \times 10^3$ cfu/0.1 ml, or between $3-17 \times 10^4$ cfu/0.1 ml, or between $3-17 \times 10^5$ cfu/0.1 ml or between $3-17 \times 10^6$ cfu/0.1 ml of the MTBVAC strain, minimizing the loss of viability after lyophilization in a development process that offered consistent results and a product with a shelf life of at least 2 years stored between 2-8° C.

In the development phase with MTBVAC, up to 7 different stabilizer compositions were tested. The following table 11 illustrates the stabilizer compositions tested:

TABLE 11

| Stabilizer | Components | Concentration |
|---|---|---|
| S | Medium (no stabilizer) | NA |
| GSA | Sodium glutamate | 10-40 g/L |

TABLE 11-continued

| Stabilizer | Components | Concentration |
|---|---|---|
| GSM | Sucrose | 100-400 g/L |
| | Sodium glutamate | 10-40 g/L |
| | Sucrose | 100-400 g/L |
| | Mannitol | 20-50 g/L |
| GSb | Glycocola | 30-200 g/L |
| | Sucrose | 100-400 g/L |
| GT | Glycocola | 30-200 g/L |
| | Trehalose | 18-60 g/L |
| GTS | Trehalose | 30-60 g/L |
| | Glycocola | 40-100 g/L |
| | Sucrose | 75-200 g/L |
| GSTG | Sodium glutamate | 10-40 g/L |
| | Glycocola | 75-150 g/L |
| | Sucrose | 75-200 g/L |
| | Trehalose | 15-60 g/L |

The following tables below 12 to 13 show the results in terms of percentage of viability loss in an accelerated stability study of laboratory-scale lyophilization tests of MTBVAC. The tables show the effect of the composition of the lyophilization medium in combination with the stabilizer in the lyophilization process. From these studies it was concluded that it is necessary to add stabilizer for the lyophilization of MTBVAC and that the GSA stabilizer is the one that offers the best results for the parameters tested.

TABLE 12

Lyophilization of MTBVAC grown in SD medium with different stabilizers. Percentage of viability loss in an accelerated stability study.

| Batch | GSA | GSB | GSM | GT | S |
|---|---|---|---|---|---|
| 001 | 73% | 97% | | >99% | |
| 005 | >99% | | | | |
| 009 | >99% | | | | >99% |
| 011 | >99% | | | | |
| 012 | >99% | | | | |
| 013 | >99% | | | >99% | >99% |
| 014 | >99% | | >99% | | |

TABLE 13

Lyophilization of MTBVAC grown in SDG medium with different stabilizers. Percentage of viability loss in an accelerated stability study.

| Batch | GSA | GSB | GSM | GTS | GT | GSTG | S |
|---|---|---|---|---|---|---|---|
| 002 | 61% | >99% | | 60% | 98% | 98% | |
| 003 | 62% | | 77% | | | | |
| 004 | 89% | | | | >99% | | >99% |
| 005 | 73% | | | | | | |
| 006 | 59% | | >99% | | | | |
| 007 | 49% | | 32% | 86% | | | |

Lastly, the following table shows the lyophilization results of 4 batches of MTBVAC:

TABLE 14

| Control | Specification | Lot 102897 | Lot 110142 | Lot 110238 | Lot 110380 |
|---|---|---|---|---|---|
| Appearance | Lyophilized pill | conform | conform | conform | conform |
| Vacuum | Complies | conformable | conformable | conformable | conformable |
| Purity (EP 2.6.1) | Absence of contamination | conformable | conformable | conformable | conformable |
| Residual moisture | <3% w/w | 1.44% | 1.26% | 1.68% | 1.84% |
| Identification (PCR) | Molecular characterization | conform | conform | conform | conform |
| Viable count (cfu/vial) | 3-17 × $10^6$ cfu/vial | 1.63 × $10^7$ | 8.54 × $10^6$ | 1.58 × $10^7$ | 8.54 × $10^6$ |
| Lyophilization loss | <90% | 64% | 67% | 63% | 67% |

Figure 3:
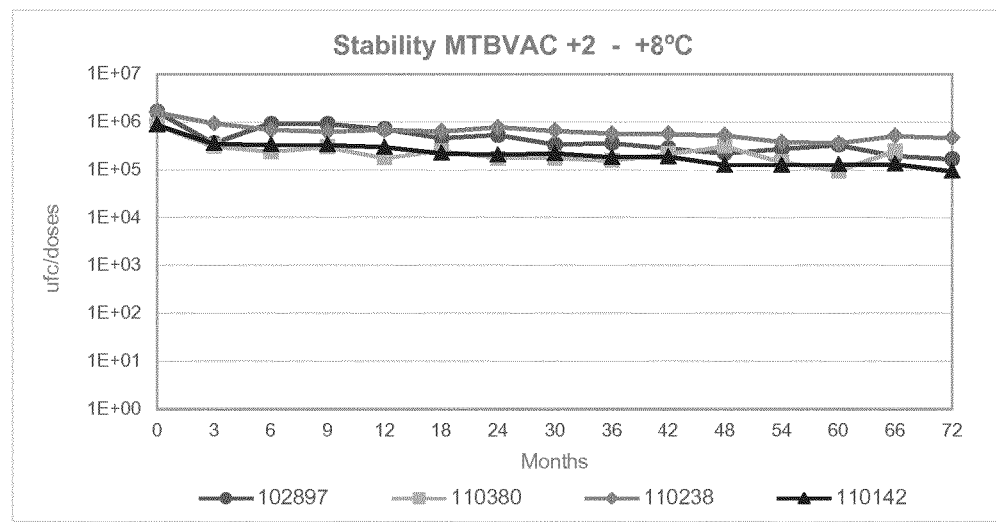
FIG. 3 shows the stability results between 2-8° C. and −30° C. of the lots or batches identified in table 15.
Figure 3:
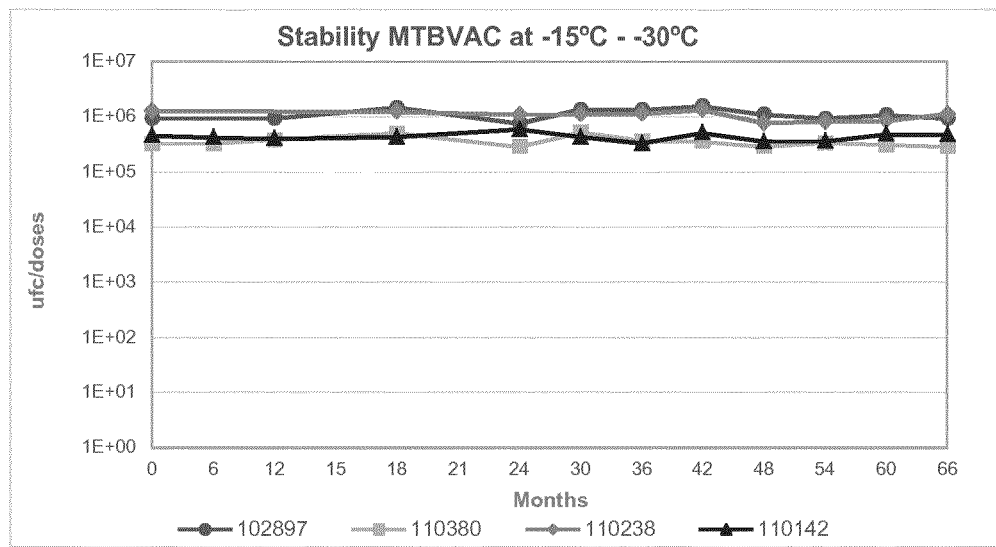

FIG. 3 shows the stability results between 2-8° C. and −30° C. of the lots or batches identified in table 14 above. Moreover, the following table 15 provides further results of parallel lyophilization of the culture of table 11 (SDG medium) in a pilot and industrial plant.

TABLE 15

| | | Lyophilization lot | | | | | |
|---|---|---|---|---|---|---|---|
| Control | Specification | 171437P | 171611In | 171889P | 171976In | 172952P | 172871IN |
| Culture lot MTBVAC | | 170928 | 170928 | 170580 | 170580 | 172547 | 172547 |
| Appearance | Lyophilized pill | conformable | conformable | conformable | conformable | conformable | conformable |
| Vacuum | Complies | conformable | conformable | conformable | conformable | conformable | conformable |
| Purity (EP 2.6.1) | Absence of contamination | conformable | conformable | conformable | conformable | conformable | conformable |
| Residual moisture | <3% w/w | 1.72 | 1.89 | 2.02 | 2.13 | 1.89 | 1.37 |
| Identification (PCR) | Molecular characterization | conformable | conformable | conformable | conformable | conformable | conformable |
| Viable count (cfu/vial) | 3-17 × $10^6$ cfu/vial | 1.5 × $10^7$ | 1.6 × $10^7$ | 6.03 × $10^7$ | 1.17 × $10^7$ | 1.03 × $10^7$ | 1.37 × $10^7$ |
| Lyophilization loss | <90% | 64% | 67% | 63% | 67% | 81.03% | 74.76% |

All of the above results were obtained by the lyophilisation of the SDG medium in which the MTBVAC strains were grown, preferably grown in the range between $1\times10^8$ to $5\times10^8$ cfu/mL. It is noted that to carry out said lyophilisation, sodium glutamate and sucrose (GSA) was added, preferably at a concentration between 10-40 g/L of sodium glutamate and between 100-400 g/L of sucrose.

Therefore, described herein are specific formulations and methods that can be used for the preparation of live MTBVAC strain-based pharmaceutical products, as described further below. The formulations of the invention comprise or consist of any of the compositions detailed below per se and these may be use for culturing MTBVAC strains. The compositions are detailed below:

| Components | Seed medium | | Medium SD | | Medium SDG | |
|---|---|---|---|---|---|---|
| L-Asparagine | 2.00-4.00 | g | 2.00-4.00 | g | 2.00-4.00 | g |
| Monopotassium phosphate | 0.30-0.60 | g | 0.30-0.60 | g | 0.30-0.60 | g |
| Magnesium sulfate H$_2$O | 0.5-0.70 | g | 0.50-0.70 | g | 0.50-0.70 | g |
| Ammonium ferric citrate | 0.02-0.05 | g | 0.02-0.05 | g | 0.02-0.05 | g |
| Dextrose monohydrate | 7.00-8.00 | g | 3.00-4.00 | g | 3.00-4.00 | g |
| Glycerol | 10.0-20.0 | mL | 30-40 | mL | 3.0-10.0 | mL |
| Citric acid | 1.5-2.0 | g | 1.5-2 | g | 1.5-2 | g |
| Polysorbate 80 | | | 0.15-0.5 | mL | 0.15-0.5 | mL |
| Purified water QS | 1.00 | L | 1.00 | L | 1.00 | L |

Thus, an eighth aspect of the invention refers to a composition comprising or consisting of the seed medium as characterized above.

A ninth aspect of the invention refers to a composition comprising or consisting of the SD medium as characterized above.

A tenth aspect of the invention refers to a composition comprising or consisting of the SDG medium as characterized above.

An eleventh aspect of the invention refers to any of the seed medium, the SD medium or the SDG medium, as characterized above, wherein said medium further comprises MTBVAC strains grown therein, preferably in the range between $1\times10^8$ to $5\times10^8$ cfu/mL.

A twelve aspect of the invention refers to the use of any of the seed medium, the SD medium or the SDG medium, as characterized above, for culturing or expanding MTBVAC strains, under aerobic conditions. In this sense, preferably as a means to start the MTBVAC strain cultures, the seed medium is selected, as a means for the amplification passages the SD medium is selected, and as a means for the mass culture before lyophilization, the SDG medium is selected. In particularly preferred embodiments of the twelve aspect of the invention, the invention refers to a process for the production of a ready to freeze-dried live-attenuated M. tuberculosis vaccine composition comprising an isolated microorganism belonging to a M. tuberculosis strain having a i) PhoP– phenotype by the inactivation by a genetic deletion of the Rv0757 gene and ii) the deletion of a second gene, Rv2930 (fadD26), that prevents PDIM production (PDIM– phenotype), much preferably the MTBVAC strain, wherein the process comprises starting the culture of the M. tuberculosis strain and expanding or amplifying said bacteria by using a suitable cell medium, wherein the process is characterized in that for the mass culture before lyophilization, a SDG medium is used. Preferably, the process comprises starting the culture of the M. tuberculosis strain in the seed medium and expanding or amplifying said bacteria by using the SD medium, and using the SDG medium for the mass culture before lyophilization. More preferably, the process further comprises a freeze-drying step by adding sucrose and sodium glutamate as stabilizers to the SDG medium used for the mass culture prior to the lyophilization step.

In addition, certain components (e.g., particular stabilizers, bulking agents, and buffers) have been found to be advantageous in the preparation of lyophilized MTBVAC strains vaccines. The invention also relates to reconstituted vaccines, and prophylactic and therapeutic methods employing the compositions described herein. The compositions and methods of the invention are described further, as follows.

In particular, a thirteenth aspect of the invention provides a live-attenuated M. tuberculosis vaccine composition comprising an isolated microorganism belonging to a M. tuberculosis strain having a i) PhoP– phenotype by the inactivation by a genetic deletion of the Rv0757 gene and ii) the deletion of a second gene, Rv2930 (fadD26), that prevents PDIM production (PDIM– phenotype), preferably the M. tuberculosis strain is the MTBVAC strain, wherein said composition is a freeze-dried composition, and wherein said composition is obtained by freeze-drying a culture medium comprising the microorganism by adding sucrose and sodium glutamate as stabilizers, and wherein the culture medium is the SDG medium. More preferably, in a thirteenth aspect, the present invention provides a live-attenuated M. tuberculosis vaccine composition comprising an isolated microorganism belonging to a M. tuberculosis strain having a i) PhoP– phenotype by the inactivation by a genetic deletion of the Rv0757 gene and ii) the deletion of a second gene, Rv2930 (fadD26), that prevents PDIM production (PDIM– phenotype), wherein preferably the M tuberculosis strain is the MTBVAC strain, and wherein said live-attenuated M. tuberculosis vaccine composition is obtained or obtainable according to the process of the twelve aspect of the invention.

Still more preferably, the present invention provides a live-attenuated M. tuberculosis vaccine composition, preferably a reconstituted composition after freeze-drying, comprising an isolated microorganism belonging to a M. tuberculosis strain having a i) PhoP– phenotype by the inactivation by a genetic deletion of the Rv0757 gene and ii) the deletion of a second gene, Rv2930 (fadD26), that prevents PDIM production (PDIM– phenotype), wherein preferably the M tuberculosis strain is the MTBVAC strain, and wherein said composition is characterized in that it comprises or consists of the following components per mL (in percentual terms):

| Components | MTBVAC Dose per 1 mL |
|---|---|
| L-Asparagine | 0.034-0.066% |
| Monopotassium phosphate | 0.006-0.010% |
| Magnesium sulfate H$_2$O | 0.008-0.012% |
| Ammonium ferric citrate | 0.0004-0.0008% |
| Dextrose monohydrate | 0.05-0.066% |
| Glycerol | 0.00005-0.0001% |
| Citric acid | 0.026-0.034% |
| Polysorbate 80 | 0.000002-0.000008% |
| Sodium glutamate | 0.33-1.33% |
| Sucrose | 3.3-13.3% |
| Purified water QS | 1 mL |

More preferably, the live-attenuated *M. tuberculosis* vaccine composition mentioned in the paragraph above is freeze-dried, or a reconstituted composition obtained by adding water, preferably sterilized water for injection, to a freeze-dried composition.

In a preferred embodiment of the thirteenth aspect of the invention or of any of its preferred embodiments, said composition is characterized in that it comprises at least $3\times10^3$ cfu per 0.1 ml, preferably per 0.1 ml of water, or more strains of the microorganism. Preferably, the composition comprises between $3\times10^4$ cfu per 0.1 ml and $17\times10^6$ cfu per 0.1 ml strains of the isolated microorganism. More preferably, the composition comprises between 3 and $17\times10^4$ cfu per 0.1 ml, or between 3 and $17\times10^5$ cfu per 0.1 ml or between 3 and $17\times10^6$ cfu per 0.1 ml strains of the isolated microorganism. Still more preferably, release specification for the freeze-dried MTBVAC vaccine comprising between 1.5 and $8.5\times10^5$ cfu/0.05 ml MTBVAC strains, is detailed in the table below

| Test | Acceptance Criteria | Methodology |
|---|---|---|
| Appearance | White freeze dried pellet | Observation |
| Vacuum | Any vial without vacuum is discarded. | Fluorescence is observed |
| Purity | Absence of bacterial and fungal contamination except for the presence of mycobacteria. | Eur. Ph. Sterility test (2.6.1) |
| Water | ≤3% w/w | Karl-Fischer method |
| Identification-PCR | Confirmation of fadD26 and phoP deletions | Real-time PCR assay |
| Viable bacterial count | $1.5\text{-}8.5 \times 10^5$ cfu/dose (0.05 ml) | Counting in specific medium |
| Loss on drying | ≤90% | Loss of viability |
| Excessive dermal reactivity | Reaction is lower than from that produced by the comparison vaccine | Eur. Ph. BCG (0163) test |
| Virulent mycobacteria | Not more than 1 from 10 animals dies during the 42 days following the injection, and autopsy does not reveal any sign of tuberculosis. | Eur. Ph. BCG (0163) test |
| Presentation | Complies | Check of the packaging |

Figure 8:
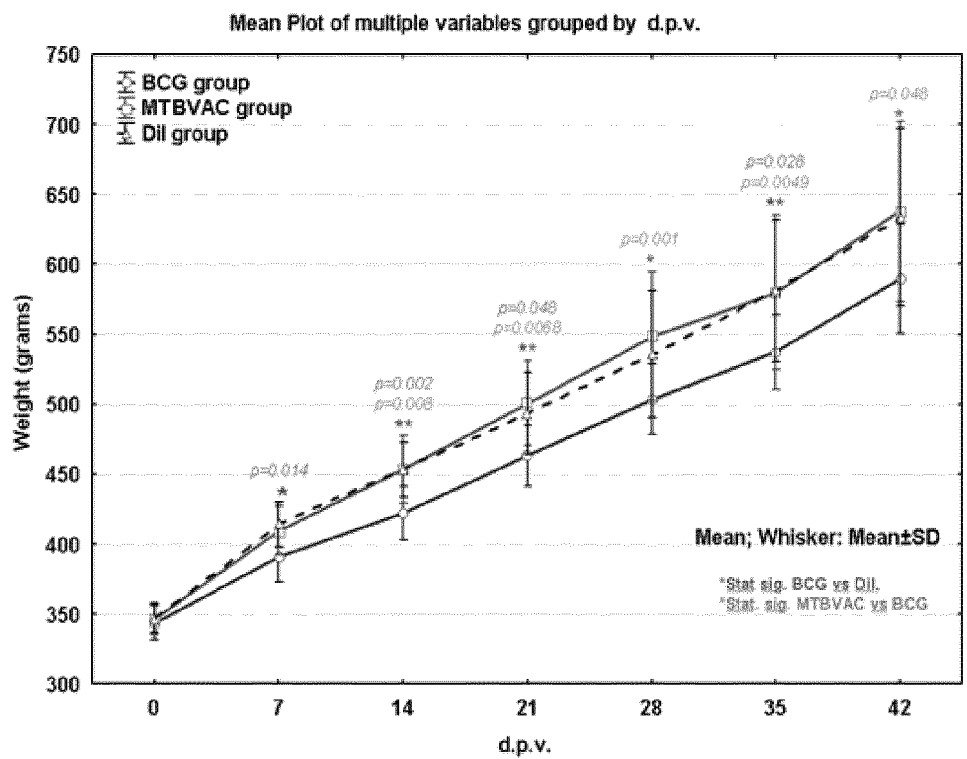
FIG. 8. Absence of virulent mycobacteria in the working seed lot in Guinea pigs.
Figure 8:
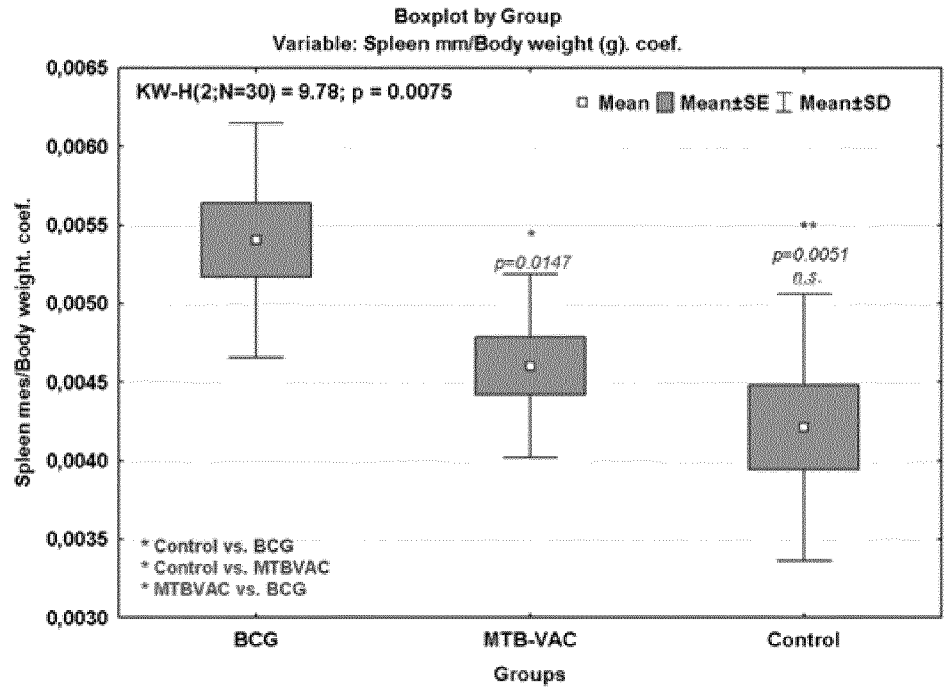
Figure 9:
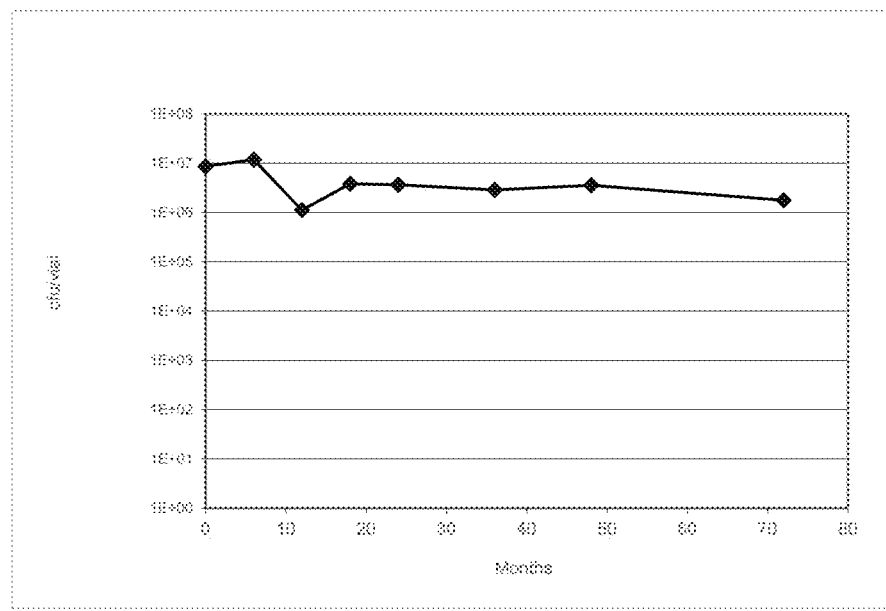
FIG. 9. Stability studies in the Master and working seed lots.
Figure 9:
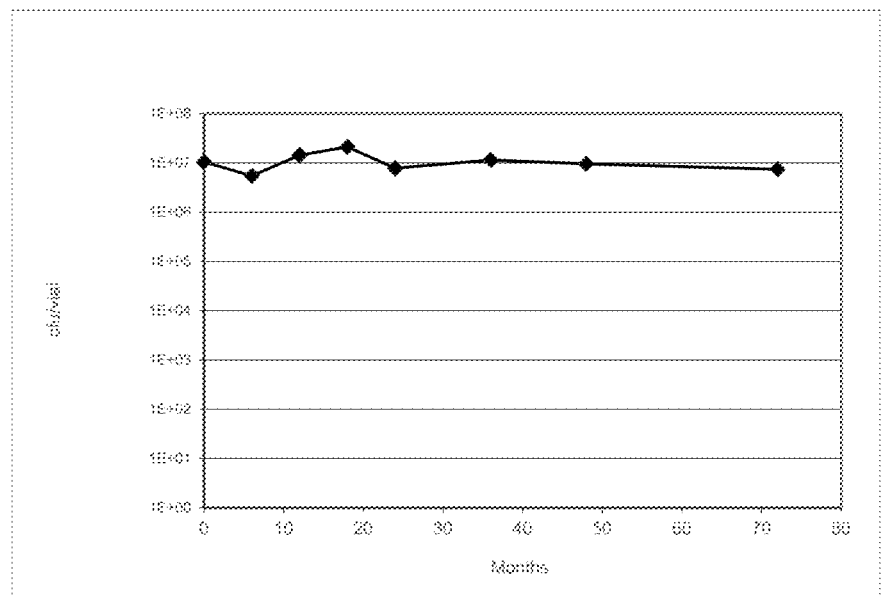
Figure 10:
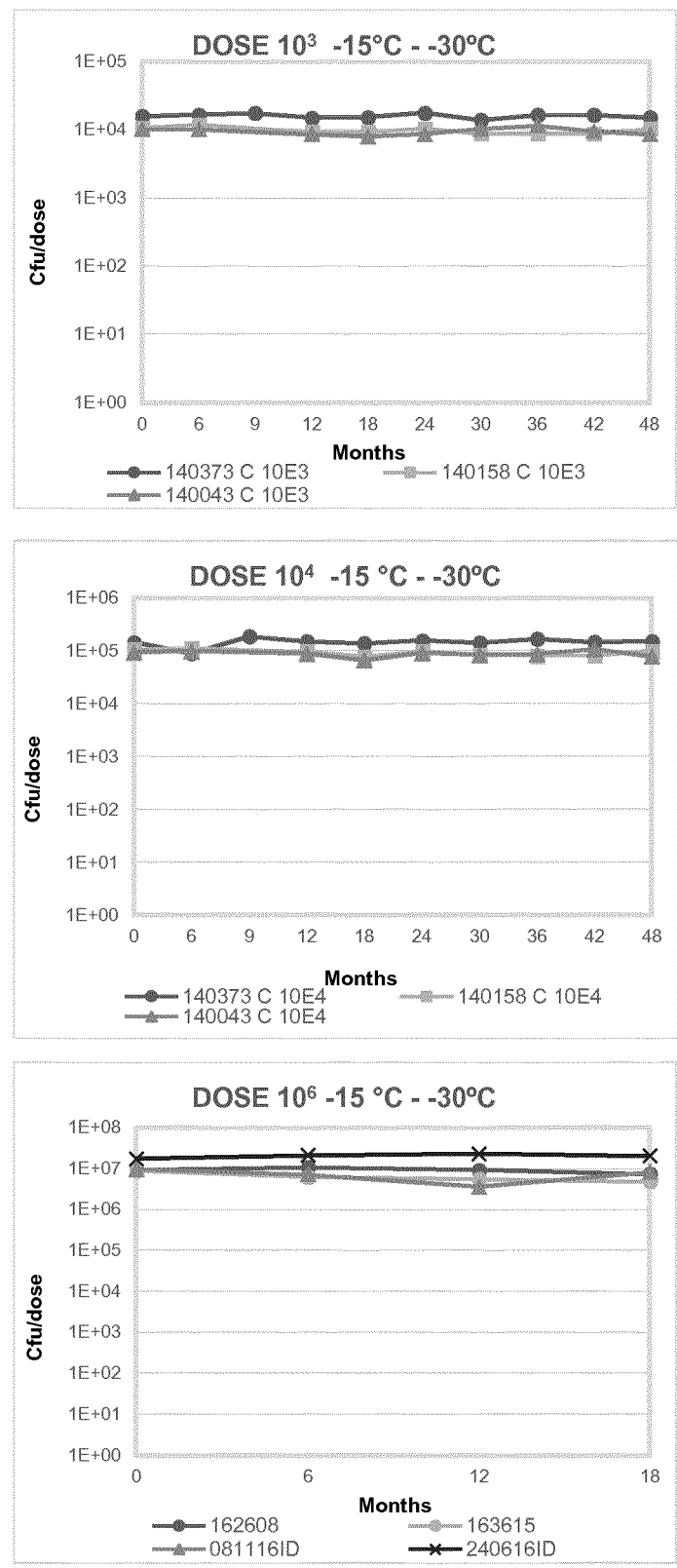
FIG. 10. Long term stability study of MTBVAC vaccine 3-17×$10^3$ cfu/0.1 mL dose, 3-17×$10^4$ cfu/0.1 mL dose and 3-17×$10^6$ cfu/0.1 mL dose stored at −15° C.--−30° C., (A), and stored at +2° C.-+8° C., (B).
Figure 10:
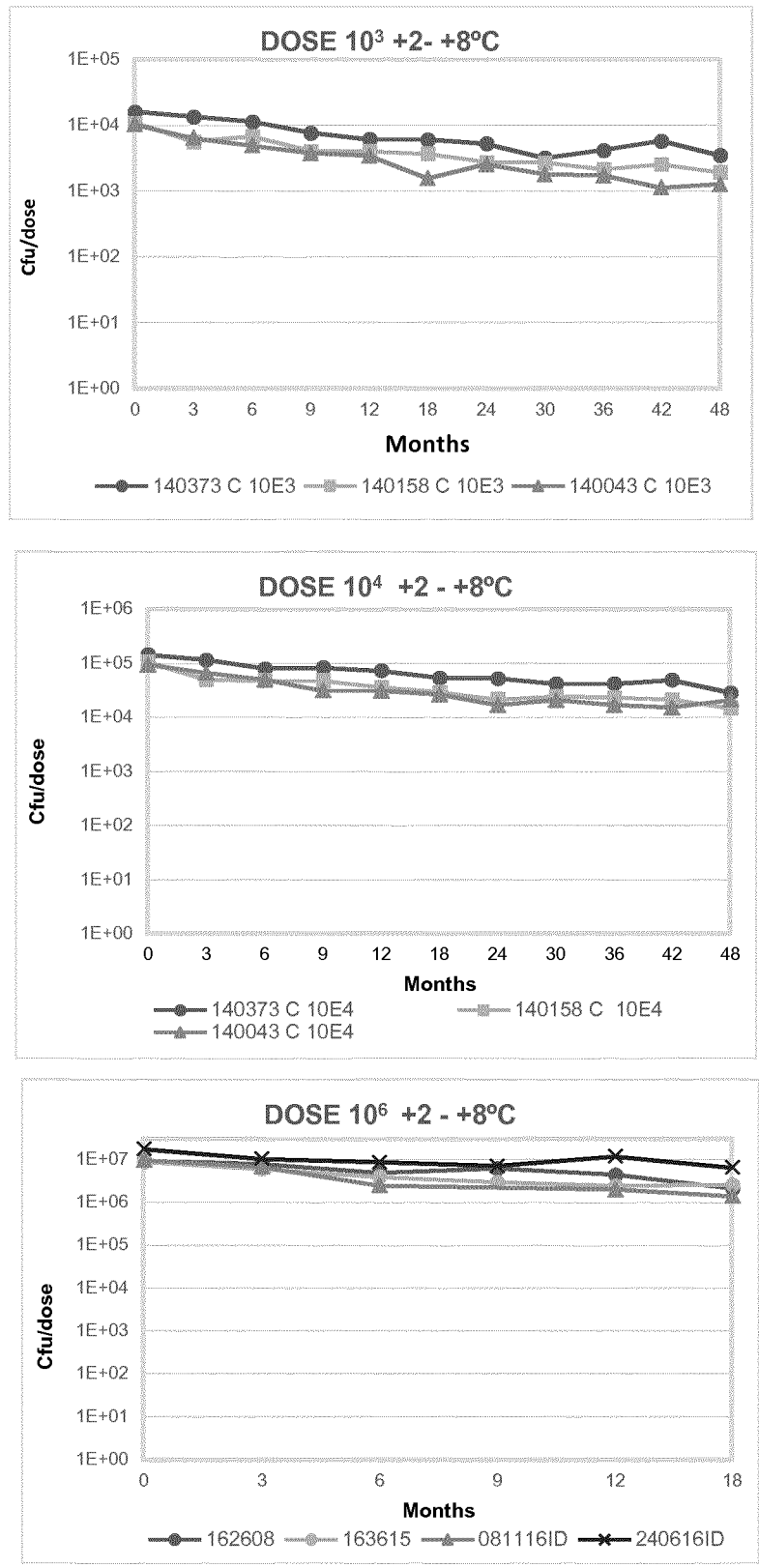

In addition, as shown in this specification, stability data demonstrates that both master and working cell banks, prepared from the Pre-master seed, are stable (see FIG. 8) and that the vaccine MTBVAC stored between −15° C.-30° C. and between +2-+8° C. is stable for more than 24 months (see FIGS. 3 and 10).

In addition, in use stability study shows that MTBVAC vaccine is stable for at least 8 hours at room temperature once it has been reconstituted.

As is discussed in further detail elsewhere herein, the compositions of the invention are particularly advantageous because of the stability and viability of the active components, which is due in large part to the formulation and the process by which the product is prepared, which involves lyophilization. In general, this process includes the following steps: freezing, primary drying, secondary drying, and stoppering. The process is described in further detail below, in the experimental examples, but an example of the process is as follows. In the freezing step, the lyophilizer shelves are pre-cooled to −50° C. Once all trays are loaded, the shelves are held at −50° C. for 120 minutes. In the primary drying step, the vacuum is set to 25 mT, and the following ramp steps are carried out: ramp at +0.1° C./minute to a shelf temperature of −40° C., hold for 500 minutes; ramp at +0.1° C./minute to a shelf temperature of −35° C., hold for 500 minutes; ramp at +0.1° C./minute to a shelf temperature of −30° C., hold for 500 minutes, and ramp at +0.1° C./minute to a shelf temperature of −25° C., hold for 800 minutes. In the secondary drying step, the vacuum remains at 25 mT, and a ramp step is carried out such that ramping is at +0.1° C./minute to a shelf temperature of +20° C., hold for 800 minutes. If necessary, the product can be held at +20° C., 25 mT up to 24 additional hours before stoppering. In the stoppering step, the chamber is outgassed with 0.22 μm filtered, dry, nitrogen gas, the vacuum is set to 800 mbar (slight vacuum), and stoppers are pushed into vials. Alternative lyophilization cycles that can be used in the invention are well known in the art. Thus, the methods of the invention can involve freezing at or to about, for example, −70° C. to −30° C. (e.g., −60° C. to −40° C., or −50° C.). The freezing can be carried out for about 30 to 240 minutes (e.g., 60 to 120 minutes) or longer. The material can then be subject to one or more drying steps, as described herein. In these steps, a vacuum can be applied (e.g., 25 mT) and the temperature can be changed gradually (e.g., 0.1 to 1.0° C./minute, or 0.5° C./minute), over the course of a period of time (such as, 100-1000 minutes, e.g., 200-600 or 300-500 minutes). In the primary drying, the temperature may be raised to or about, for example, −30° C. to +10° C., e.g., −20° C. to +5° C. or −15° C. to 0° C., while in the secondary drying, the temperature may be changed to, for example, +5° C. to +35° C., e.g., 10° C. to 30° C., or 15° C. to 20° C. As is known to those skilled in this art, these parameters (e.g., temperatures, hold times, ramp rates, and vacuum levels) can be changed based on, for example, results obtained.

The vaccine compositions of the thirteenth aspect of the invention can be administered, according to a fourteenth aspect of the invention, as primary prophylactic agents to those at risk of infection with *M. tuberculosis* or those at risk of developing tuberculosis disease, or can be used as secondary agents for treating infected patients. Because the strains of these compositions are attenuated, they are particularly well suited for administration to "at risk individuals" such as newborns, children, adolescents, adults, and elderly. Such vaccines can also be used in veterinary contexts.

A preferred embodiment of the fourteenth aspect of the invention relates to the MTBVAC vaccine for immunizing an individual against the symptoms caused by tuberculosis. It is noted that said vaccine may be also suitable for the treatment of bladder cancer as well as for the treatment or prevention of TB, or as a vector or adjuvant. Preferably to immunize an individual against the symptoms caused by TB.

In another preferred embodiment of the fourteenth aspect of the invention, the composition of the thirteenth aspect is administered for prophylaxis in neonates at risk of infection with *M tuberculosis* or those at risk of developing TB disease, against infections caused by *M. tuberculosis* complex, preferably *M. tuberculosis*. More preferably, said composition is administered via the intradermal route to the neonates.

In another preferred embodiment of the fourteenth aspect of the invention, the composition of the thirteenth aspect is administered for prophylaxis or prevention (including booster vaccination) in non-neonate humans, such as children, adolescents and adults at risk of infection with *M tuberculosis*, against infections caused by *M. tuberculosis* complex, preferably *M. tuberculosis*. More preferably, said composition is administered via the intradermal route.

In another preferred embodiment of the fourteenth aspect of the invention, the composition of the thirteenth aspect is administered for prophylaxis or prevention in non-neonate humans, such as children, adolescents and adults at risk of developing TB disease and suffering from latent tuberculosis infection, against the development of the clinical symptomatology associated with the active form of the disease caused by M. tuberculosis complex, preferably M. tuberculosis. More preferably, said composition is administered via the intradermal route.

In another preferred embodiment of the fourteenth aspect of the invention, the composition of the thirteenth aspect is administered for use as a secondary agent for treating patients infected with latent and/or active TB in neonates and non-neonate humans, such as children, adolescents and adults. More preferably, said composition is administered via the intradermal route.

In another preferred embodiment of the fourteenth aspect of the invention, the composition of the thirteenth aspect is administered for booster vaccination or booster dose in a prophylactic or preventive treatment in non-neonate humans, such as children, adolescents and adults at risk of infection with M. tuberculosis, against infections caused by M. tuberculosis complex, preferably M. tuberculosis. In this sense, it is noted that after initial immunization, a booster injection or booster dose is a re-exposure to the immunizing antigen. It is intended to increase immunity against that antigen back to protective levels, after memory against that antigen has declined through time.

Throughout the description and claims the word "comprise" and its variants do not imply the exclusion of other technical characteristics, additives, components or steps. For a person skilled in the art, other objects, advantages and characteristics of the invention will arise partly out of the description and partly when the invention is put into practice. The following examples and figures are provided by way of a non-limiting, illustrative example of the present invention.

EXAMPLES

Example 1. Immunogenicity and Protection are Independent of the Dose of MTBVAC in Newborn Mice Newborn C3H mice (1-to-3 days old) were vaccinated intradermally with 25 µl containing one clinical dose of BCG ($2.5 \times 10^5$ aprox), or the indicated CFU dosages of MTBVAC. For BCG groups, commercial vials of BCG Danish were used, corresponding to lots 111053F and 113033C. In the case of MTBVAC, animals were immunized with the MTBVAC vaccine produced by the lyophilisation of the SDG medium in which the MTBVAC strains were grown, to carry out said lyophilisation, sodium glutamate and sucrose (GSA) was added at a concentration between 10-40 g/L of sodium glutamate and between 100-400 g/L of sucrose. Lyophilized formulations were resuspended.

Protective Efficacy Studies

Figure 4:
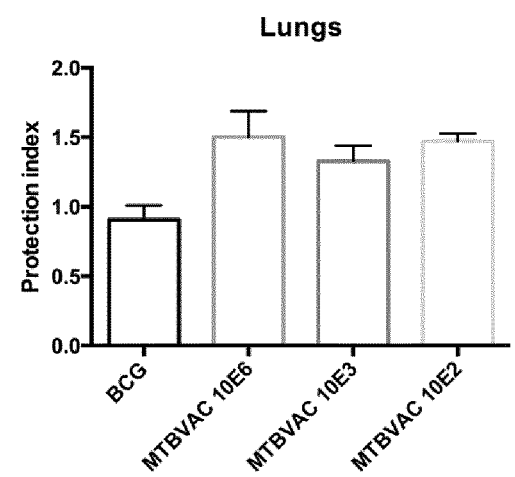
FIG. 4 Protection in mice. Data in the figure represent a pool of two independent experiments (n=12 mice/group). All data are mean±SEM. Protection index is defined as the difference between bacterial load in unvaccinated and vaccinated groups (represented in decimal logarithm).

Eight weeks post-vaccination, mice were challenged intranasally with 150 CFU of M. tuberculosis strain H37Rv. Four weeks later, mice were sacrificed and bacterial burden was determined in lungs by tissue homogenate plating on 7H11S solid medium. The results are shown in FIG. 4.

Immunogenicity Studies

Figure 5:
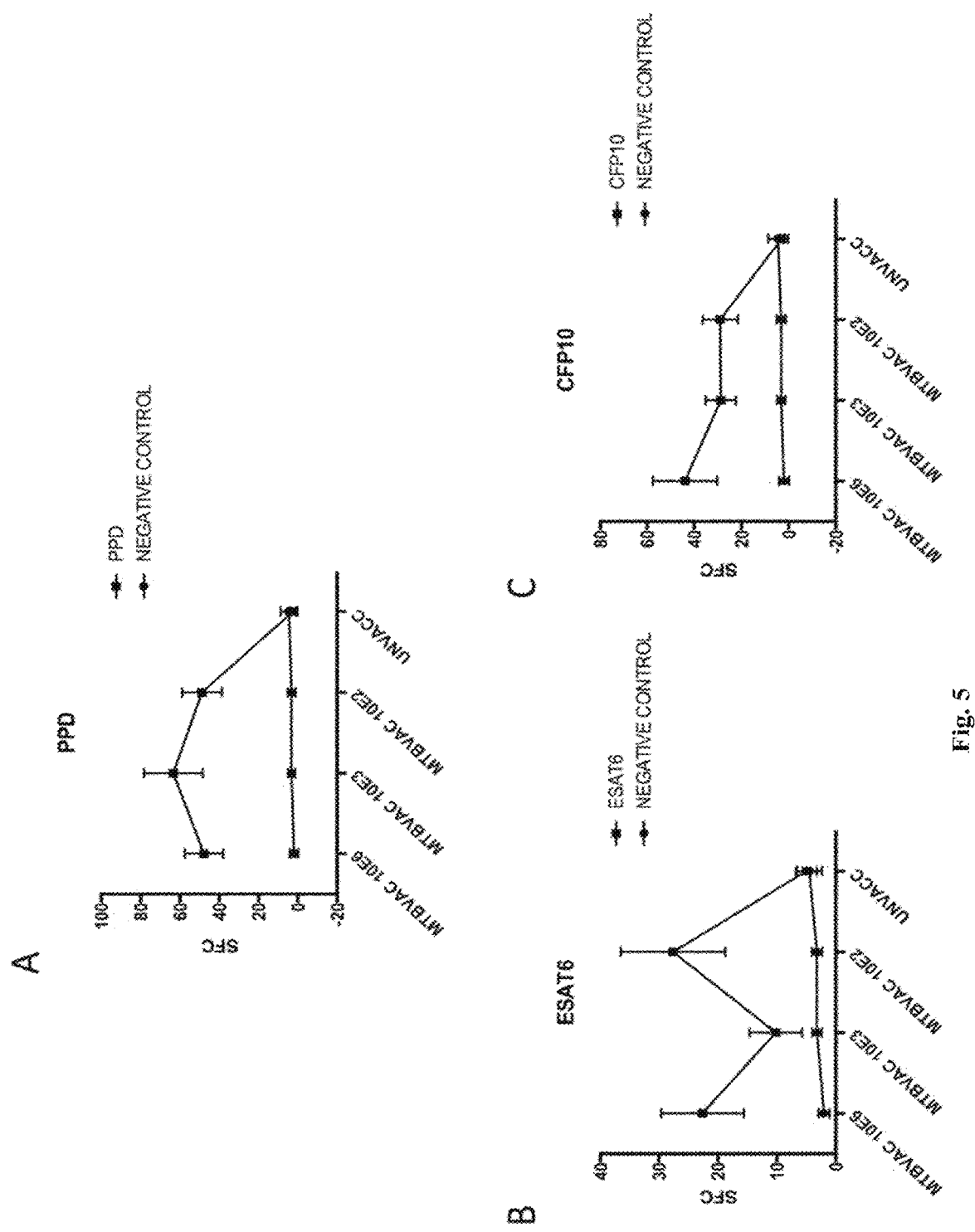
FIG. 5. Immunogenicity in mice. Data in the figure are from one experiment (n=5 mice/group). All data are mean±SEM. SFC: Spot Forming Colony.

Eight weeks post vaccination, mice were sacrificed and splenocytes isolated for immunogenicity assessment. One million of splenocytes were incubated 24 hours in the presence of 10 µg/ml of Purified Protein Derivative (PPD), 2 µg/ml of overlapping ESAT6 or CFP10 peptides, or non-antigen (negative control). Interferon gamma (IFNγ) producing cells were analyzed by ELISPOT. The results are shown in FIG. 5.

Conclusion

Neither protective efficacy nor immunogenicity specific for PPD, ESAT6 or CFP10 induced by MTBVAC was shown to be dose dependent in the newborn mouse model.

Example 2. Phase 1B Immunogenicity Data in Newborns (South Africa)

Objective: We sought to determine immunogenicity and characterize induced immune responses after neonatal vaccination with the MTBVAC vaccine described in the present invention.

Methods: Thirty-six HIV-unexposed, BCG-naïve healthy newborns were randomized 1:3 to receive either BCG (strain SSI) or MTBVAC at $2.5 \times 10^3$, $2.5 \times 10^4$, or $2.5 \times 10^5$ CFU within 96 h of birth. MTBVAC-specific cytokine responses in whole blood were measured on days 7, 28, 70 by whole blood intracellular cytokine staining and flow cytometry on a BD LSRFortessa (18 colour, blue-red-violet-green configuration).

Narrative for Whole Blood ICS Assay:

Fresh whole heparinized bloods were stimulated immediately with BCG, MTBVAC, or phytohemagglutinin (PHA) or were left unstimulated (Nil), for 12 hours at 37° C. Stimulation conditions include half the blood volume [250 µL (0.25 ml)] and only Nil, MTBVAC and BCG. After 7 hours of stimulation, supernatant (for soluble cytokine/chemokine analysis) were collected from all the conditions, frozen at −BOC and stored for shipping to Sponsor for further analysis. Following supernatant removal, brefeldin A was added for the remaining whole blood and tubes incubated for a further 5 hrs in a programmable water bath. The water bath will switch off after a total of 12 hours of stimulation. The next morning, FACS Lysing solution was added to lyse red cells and fix white cells. Fixed, white cells were then frozen for later intracellular cytokine staining and flow cytometry. Flow cytometric staining and acquisition will be run in batches at a later time point. Measurement of frequencies and patterns of specific type-1 cytokines and IL-17 by CD4 T cells were assessed. The timepoints for immunogenicity have been selected on the basis of recent studies conducted by SATVI, which have shown that the peak of the BCG-induced T cell responses in infants is around 6-10 weeks of age.

Figure 6:
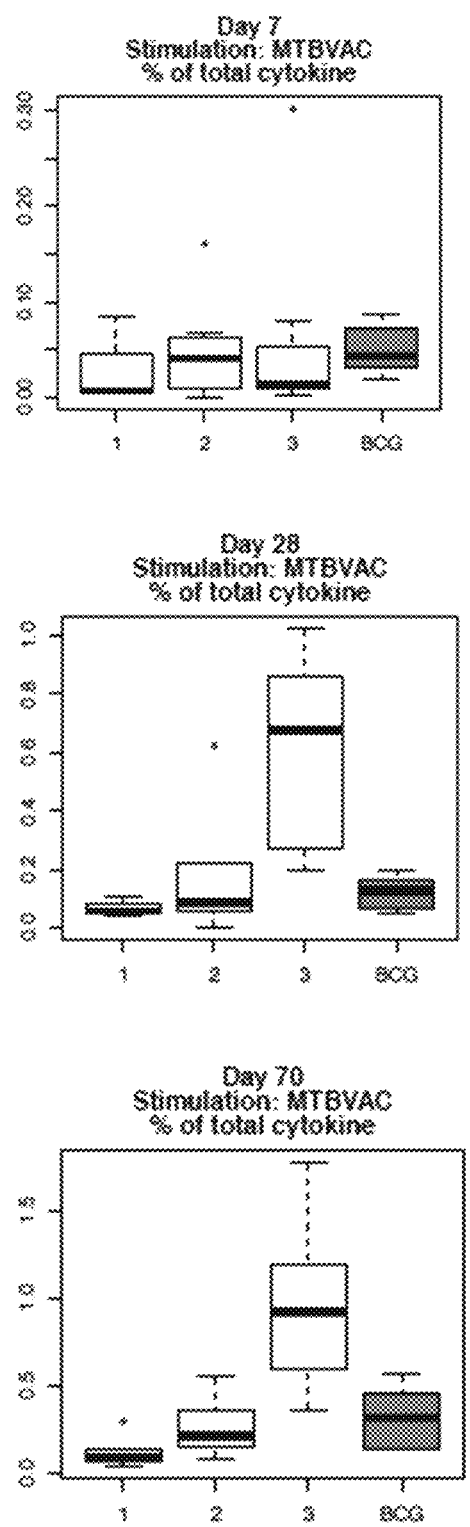
FIG. 6. Vaccination of neonates from a TB endemic setting with escalating doses of MTBVAC resulted in predominantly Th1 (IFN-γ, IL-2, or TNF-α) antigen-specific CD4 T-cell responses. The highest MTBVAC dose of 2.5× $10^5$ CFU induced the greatest magnitude of antigen-specific CD4 T-cells cytokine response at day 70. The lowest MTB-VAC dose of 2.5×$10^3$ CFU was the least immunogenic.

Results: Vaccination with escalating doses of MTBVAC resulted in predominantly Th1 (IFN-γ, IL-2, or TNF-α) antigen-specific CD4 T-cell responses. The highest MTBVAC dose of $2.5 \times 10^5$ CFU induced the greatest magnitude antigen-specific CD4 T-cells cytokine response at day 70. The lowest MTBVAC dose of $2.5 \times 10^3$ CFU was the least immunogenic. Results are further illustrated in FIG. 6.

Conclusions: These data indicate that vaccination with MTBVAC at $2.5 \times 10^4$ or $2.5 \times 10^5$ or more CFU are immunogenic in neonates from a TB endemic setting.

Example 3

A randomized, double-blind, dose-escalation clinical trial of MTBVAC compared to BCG Vaccine SSI, and newborns with a safety arm in adults in a living in a TB endemic region Objectives. Evaluation of safety and immunogenicity of 3 doses of MTBVAC vs BCG in newborns in a TB endemic region.

Methods Eighteen HIV-, QuantiFERON (QFT)-, previously BCG vaccinated healthy adults were randomized 1:1 to receive MTBVAC ($5\times10^5$ CFU) or BCG SSI. Thereafter, 36 HIV-unexposed, BCG-naïve healthy newborns were randomized 1:3 to receive BCG SSI or MTBVAC at $2.5\times10^3$, $2.5\times10^4$, or $2.5\times10^5$ CFU within 96 h of birth. QFT was performed at D180 and D360 and QFT+ infants (>0.35 IU/mL) were referred for isoniazid preventive therapy.

Results All adults experienced local injection site reactions with swelling in 18(100%), redness in 16 (88.9%) and ulceration in 10 (55.5%). Nine reactions were reported as moderate and a single swelling event was severe (35 mm). No SAEs were reported at D28.

Unavailability of BCG Vaccine SSI resulted in open-label dosing of 6 infants with MTBVAC at the highest dose. Sixteen (44.4%) infants across all 3 cohorts had local reactions 2[16.6%], 3 [25%] and 11[91.6%]), all rated mild with swelling in 14 (38.9%), erythema in 5 (13.9%) and scarring in 9(25.0%). No ulceration was seen. Systemic AEs were similar across cohorts (n=32/42/40) with 9 graded moderate (n=3/4/2) and 8 severe (n=4/2/2). Six infants experienced 7 unrelated SAEs including an unrelated death due to viral pneumonia, confirmed by autopsy.

Figure 7:
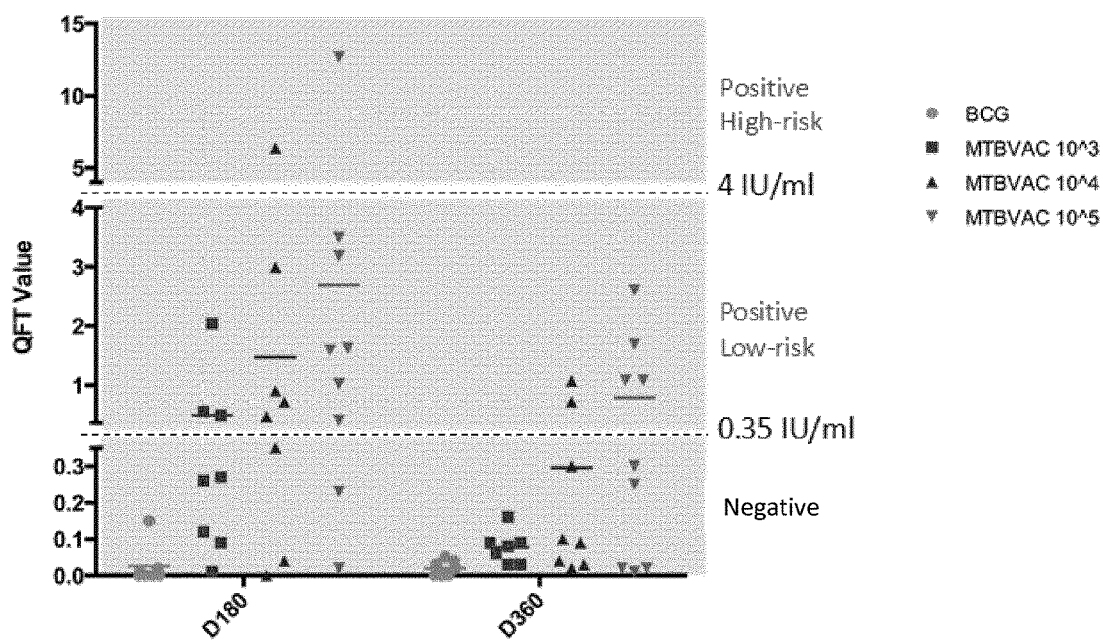
FIG. 7. Vaccination of neonates from a TB endemic setting with escalating doses of MTBVAC resulted in a dose-response profile of the quantitative value of the QFT assay at day 180 and 360 post-vaccination. The QFT values are stratified in three different regions according to the risk of developing active TB as per Andrews J R, Nemes E, Tameris M et al. Serial QuantiFERON testing and tuberculosis disease risk among young children: an observational cohort study. *Lancet Respir Med*, (2017).

Dose-related QFT conversion was noted at D180 in MTBVAC recipients in Cohort 1: (n=3, 37.5%), Cohort 2 (n=6, 75%) and Cohort 3 (n=7, 77.8%), but in zero of 7 BCG recipients. A positive QFT at D360 was seen in 0 Cohort 1 MTBVAC recipients (0.0%), 2 in Cohort 2 (25.0%) and 4 in Cohort 3 (44.4%) as illustrated in FIG. 7.

Conclusion MTBVAC appeared safe at 3 dose levels in South African newborns; and appeared to result in transient dose-dependent QFT conversion, which may be an encouraging indicator of immunogenicity in TB endemic regions. In addition, the reactogenicity of the MTBVAC vaccine was clearly lower than the reactogenicity produced with the BCG vaccine, wherein administration of the BCG vaccine in 5 out of 8 (62%) newly born produces scars, while MTBVAC at its highest dose produced scars in only 2 out of 10 (20%) newly born.

The invention claimed is:

1. A process for the production of a live-attenuated *M. tuberculosis* vaccine composition comprising an isolated bacterium belonging to a *M. tuberculosis* MTBVAC strain having a i) PhoP– phenotype by the inactivation by a genetic deletion of the Rv0757 gene, wherein the open-reading frame (ORF) sequence of PhoP consists of SEQ ID NO: 4, and ii) the deletion of a second gene, Rv2930 (fadD26), that prevents PDIM production (PDIM– phenotype), wherein the open-reading frame (ORF) sequence of fadD26 consists of SEQ ID NO: 2; wherein the process comprises starting a culture of the MTBVAC strain in a seed medium as defined in the table below; expanding or amplifying the bacterium in a SD medium as defined in the table below:

| Components | Seed medium | Medium SD |
|---|---|---|
| L-Asparagine | 2.00-4.00 g | 2.00-4.00 g |
| Monopotassium phosphate | 0.30-0.60 g | 0.30-0.60 g |
| Magnesium sulfate H$_2$O | 0.5-0.70 g | 0.50-0.70 g |
| Ammonium ferric citrate | 0.02-0.05 g | 0.02-0.05 g |
| Dextrose monohydrate | 7.00-8.00 g | 3.00-4.00 g |
| Glycerol | 10.0-20.0 mL | 30-40 mL |
| Citric acid | 1.5-2.0 g | 1.5-2 g |
| Polysorbate 80 | | 0.15-0.5 mL |
| Purified water QS | 1.00 L | 1.00 L; | growing the bacterium for mass culture in a SDG medium as defined in the table below:

| Components | Medium SDG |
|---|---|
| L-Asparagine | 2.00-4.00 g |
| Monopotassium phosphate | 0.30-0.60 g |
| Magnesium sulfate H$_2$O | 0.50-0.70 g |
| Ammonium ferric citrate | 0.02-0.05 g |
| Dextrose monohydrate | 3.00-4.00 g |
| Glycerol | 3.0-10.0 mL |
| Citric acid | 1.5-2 g |
| Polysorbate 80 | 0.15-0.5 mL |
| Purified water QS | 1.00 L | wherein the process is conducted under aerobic conditions.

2. The process of claim 1, further comprising performing a lyophilization step on the bacterium grown in the SDG medium.

3. The process of claim 2, comprising, prior to the lyophilization step, adding sucrose and sodium glutamate as stabilizers to the SDG medium used for mass culture of the bacterium.

4. The process of claim 1, wherein the bacterium is grown to a range between $1\times10^8$ to $5\times10^8$ cfu/mL in the SDG medium.

5. The process of claim 3, wherein sodium glutamate at a concentration between 10-40 g/L and sucrose at a concentration between 100-400 g/L are added to the SDG medium.

* * * * *

SEQUENCE LISTING

```
<160> NUMBER OF SEQ ID NOS: 4

<210> SEQ ID NO 1
<211> LENGTH: 1752
<212> TYPE: DNA
<213> ORGANISM: Mycobacterium tuberculosis
<220> FEATURE:
<221> NAME/KEY: misc_feature
<222> LOCATION: (1)..(1752)
<223> OTHER INFORMATION: wild-type fadD26 gene in Mt103

<400> SEQUENCE: 1
atgccggtga ccgaccgttc agtgccctct ttgctgcaag agagggccga ccagcagcct      60
gacagcactg catatacgta catcgactac ggatccgacc ccaagggatt tgctgacagc     120
ttgacttggt cgcaggtcta cagtcgtgca tgcatcattg ctgaagaact caagttatgc     180
gggttacccg gagatcgagt ggcggtttta gcgccacaag gactggaata tgtccttgca     240
ttcctgggcg cacttcaggc tggatttatc gcggttccgc tgtcaactcc acagtatggc     300
attcacgatg accgcgtttc tgcggtgttg caggattcca agccggtagc cattctcacg     360
acttcgtccg tggtaggcga tgtaacgaaa tacgcagcca gccacgacgg gcagcctgcc     420
ccggtcgtag ttgaggttga tctgcttgat ttggactcgc cgcgacagat gccggctttc     480
tctcgtcagc acaccggggc ggcttatctc caatacacgt ccggatcgac gcgtacgccg     540
gccggagtca ttgtgtcgca cacgaatgtc attgccaatg tgacacaaag tatgtacggc     600
tatttcggcg atcccgcaaa gattccgacc gggactgtgg tgtcgtggct gcctttgtat     660
cacgatatgg gcctgattct cggaatttgc gcaccgctgg tggcccgacg ccgcgcgatg     720
ttgatgagcc caatgtcatt tttgcgccgt ccggcccgct ggatgcaact gcttgccacc     780
agcggccggt gcttttctgc ggcaccgaat ttcgccttcg agctggccgt gcgcagaaca     840
tctgaccagg acatggcggg gctcgacctg cgcgacgtgg tcggcatcgt cagtggcagt     900
gagcgaatcc atgtggcaac cgtgcggcgg ttcatcgagc ggttcgcgcc gtacaatctc     960
agccccaccg cgatacggcc gtcgtacggg ctcgcggaag cgaccttata tgtggcagct    1020
cccgaagccg gcgccgcgcc caagacggtc cgttttgact acgagcagct gaccgccggg    1080
caggctcggc cctgcggaac cgatgggtcg gtcggcaccg aactgatcag ctacggctcc    1140
cccgacccat cgtctgtgcg aatcgtcaac ccggagacca tggttgagaa tccgcctgga    1200
```

```
gtggtcggtg agatctgggt gcatggcgac cacgtgacta tggggtattg gcagaagccg      1260
aagcagaccg cgcaggtctt cgacgccaag ctggtcgatc ccgcgccggc agccccggag      1320
gggccgtggc tgcgcaccgg cgacctgggc gtcatttccg atggtgagct gttcatcatg      1380
ggccgcatca aagacctgct catcgtggac gggcgcaacc actacccga cgacatcgag       1440 gcaacgatcc aggagatcac cggtggacgg gccgcggcga tcgcagtgcc cgacgacatc      1500
accgaacaac tggtggcgat catcgaattc aagcgacgcg gtagtaccgc cgaagaggtc      1560
atgctcaagc tccgctcggt gaagcgtgag gtcacctccg cgatatcgaa gtcacacagc      1620
ctgcgggtgg ccgatctcgt tctggtgtca cctggttcga ttcccatcac caccagcggc      1680
aagatccggc ggtcagcctg cgtcgaacgc tatcgcagcg acggcttcaa gcggctggac      1740
gtagccgtat ga                                                          1752

<210> SEQ ID NO 2
<211> LENGTH: 410
<212> TYPE: DNA
<213> ORGANISM: Mycobacterium tuberculosis
<220> FEATURE:
<221> NAME/KEY: misc_feature
<222> LOCATION: (1)..(410)
<223> OTHER INFORMATION: fadD26 in MTBVAC

<400> SEQUENCE: 2
atgccggtga ccgaccgttc agtgccctct ttgctgcaag agagggccga ccagcagcct       60
gacagcactg catatacgta catcgactac ggatccacta gttctagagc aaccgtccga      120
aatattataa attatcgcac acataaaaac agtgctgtta atgtgtctat taaatcgatt      180
ttttgttata acagacactg cttgtccgat atttgattta ggatacattt ttatgagatc      240
ccccgggctg caggaattcg atatcgaagt cacacagcct gcgggtggcc gatctcgttc      300
tggtgtcacc tggttcgatt cccatcacca ccagcggcaa gatccggcgg tcagcctgcg      360
tcgaacgcta tcgcagcgac ggcttcaagc ggctggacgt agccgtatga                 410

<210> SEQ ID NO 3
<211> LENGTH: 744
<212> TYPE: DNA
<213> ORGANISM: Mycobacterium tuberculosis
<220> FEATURE:
<221> NAME/KEY: misc_feature
<222> LOCATION: (1)..(744)
<223> OTHER INFORMATION: wild-type phoP gene in Mt103

<400> SEQUENCE: 3
atgcggaaag gggttgatct cgtgacggcg ggaaccccag gcgaaaacac cacaccggag       60
gctcgtgtcc tcgtggtcga tgatgaggcc aacatcgttg aactgctgtc ggtgagcctc      120
aagttccagg gctttgaagt ctacaccgcg accaacgggg cacaggcgct ggatcgggcc      180
cgggaaaccc ggccggacgc ggtgatcctc gatgtgatga tgcccgggat ggacggcttt      240
ggggtgctgc gccggctgcg cgccgacggc atcgatgccc ggcgttgtt cctgacggcc       300 cgtgactcgc tacaggacaa gatcgcgggt ctgacctggt ggtgacga ctatgtgaca        360 aagcccttca gtttggagga ggtcgtgcc aggctgcggg tcatcctgcg acgcgcgggc       420
aagggcaaca aggaaccacg taatgttcga ctgacgttcg ccgatatcga gctcgacgag      480
gagacccacg aagtgtggaa ggcgggccaa ccggtgtcgc tgtcgcccac cgaattcacc      540
ctgctgcgct atttcgtgat caacgcgggc accgtgctga gcaagcctaa gattctcgac      600
cacgtttggc gctacgactt cggtggtgat gtcaacgtcg tcgagtccta cgtgtcgtat      660
```

```
-continued ctgcgccgca agatcgacac tggggagaag cggctgctgc acacgctgcg cggggtgggc        720
tacgtactgc gggagcctcg atga                                              744

<210> SEQ ID NO 4
<211> LENGTH: 819
<212> TYPE: DNA
<213> ORGANISM: Mycobacterium tuberculosis
<220> FEATURE:
<221> NAME/KEY: misc_feature
<222> LOCATION: (1)..(819)
<223> OTHER INFORMATION: phoP in MTBVAC

<400> SEQUENCE: 4
atgcggaaag gggttgatct cgtgacggcg ggaacccag gcgaaaacac cacaccggag          60
gctcgtgtcc tcgtggtcga tgatgaggcc aacatcgttg aactgctgtc ggtgagcctc        120
aagttccagg gctttgaagt ctacaccgcg accaacgggg cacaggcgct ggatcgggcc        180
cgggaaaccc ggccggacgc ggtgatcctc gatgtgatga tgcccgggat ggacggcttt        240
ggggtgctgc gccggctgcg cgccgacggc atcgatgccc cggcgttgtt cctgacggcc        300
cgtgactcgc tacaggacaa gatcgcgggt ctgaccctgg gtggtgacga ctatgtgaca        360
aagcccttca gtttggagga ggtcgtggcc aggctgcggg tcatcctgcg acgcgcgggc        420
aagggcaaca aggaaccacg taatgttcga ctgacgttcg ccgatatcga attcctgcag        480
cccgggggat ctcataaaaa tgtatcctaa atcaaatatc ggacaagcag tgtctgttat        540
aacaaaaaat cgatttaata gacacattaa cagcactgtt tttatgtgtg cgataattta        600
taatatttcg gacggttgct ctagaactag tggatcaacg cgggcaccgt gctgagcaag        660
cctaagattc tcgaccacgt ttggcgctac gacttcggtg gtgatgtcaa cgtcgtcgag        720
tcctacgtgt cgtatctgcg ccgcaagatc gacactgggg agaagcggct gctgcacacg        780
ctgcgcgggg tgggctacgt actgcgggag cctcgatga                              819
```